United States Patent [19]

Romine et al.

[11] Patent Number: 5,348,969
[45] Date of Patent: * Sep. 20, 1994

[54] DIPHENYLOXAZOLYL-OXAZOLES AS PLATELET AGGREGATION INHIBITORS

[75] Inventors: Jeffrey L. Romine, Meriden; Nicholas A. Meanwell, East Hampton, both of Conn.

[73] Assignee: Bristol-Myers Squibb Company, New York, N.Y.

[ * ] Notice: The portion of the term of this patent subsequent to Oct. 19, 2010 has been disclaimed.

[21] Appl. No.: 862,902

[22] Filed: Apr. 3, 1992

[51] Int. Cl.$^5$ ............................................. A61K 31/42
[52] U.S. Cl. ..................... 514/376; 514/374; 548/110; 548/232; 548/235; 548/236
[58] Field of Search ................. 514/374, 376; 548/236, 548/235, 232

[56] References Cited

U.S. PATENT DOCUMENTS 3,578,670  5/1971  Brown .............................. 548/236

(List continued on next page.)

FOREIGN PATENT DOCUMENTS 0129059  12/1984  European Pat. Off. ............ 548/235
0434034  6/1991  European Pat. Off. ............ 548/236
1249760  10/1989  Japan ................................... 548/235

OTHER PUBLICATIONS

Aldous et al. J. Org. Chem. vol. 25 pp. 1151–1154 (1960).

(List continued on next page.)

*Primary Examiner*—Donald G. Daus
*Attorney, Agent, or Firm*—Prabodh I. Almaula

[57] ABSTRACT

A novel series of oxazole derivatives having enhanced water solubility bioavailability and metabolic stability is disclosed in the Formula I

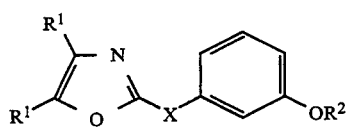

wherein

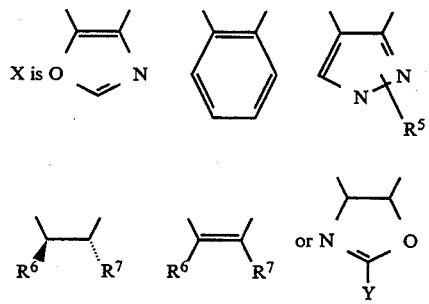

$Y$ is $CH_3$, Ph, or OH, provided that when $Y$ is OH, the compound exists in the keto-enol tautaumerism form

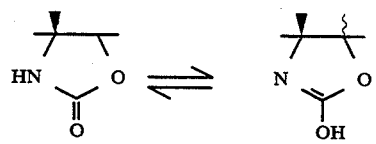

$R^1$ is Ph or Th;
$R^2$ is H or $CH_2R^3$;
$R^3$ is H, $OCH_3$, $C_1$–$C_5$ lower alkyl, or $CO_2R^4$;
$R^4$ is H or $C_1$–$C_5$ lower alkyl;
$R^5$ is H or $CH_3$;
$R^6$ is OHCHN or $H_2N$; and
$R^7$ is H or OH;

or pharmaceutically acceptable salt thereof.

The compounds are useful as inhibitors of ADP-induced blood platelet aggregation in human platelet-rich plasma.

30 Claims, No Drawings

U.S. PATENT DOCUMENTS

| | | | |
|---|---|---|---|
| 4,105,790 | 8/1978 | Hughes et al. | 548/236 |
| 4,460,598 | 7/1984 | Lautenschlager et al. | 548/336 |
| 4,659,728 | 4/1987 | Lewis et al. | 548/236 |
| 4,774,253 | 9/1988 | Machin et al. | 514/374 |
| 4,785,012 | 11/1988 | Crews et al. | 514/374 |
| 4,791,124 | 12/1988 | Lutomski et al. | 548/236 |
| 4,880,804 | 11/1989 | Carini | 514/374 |
| 5,011,851 | 4/1991 | Meanwell et al. | 514/398 |
| 5,071,988 | 12/1991 | Failli et al. | 548/236 |
| 5,262,540 | 11/1993 | Meanwell | 548/236 |

OTHER PUBLICATIONS

Lautenschlager, et al., *Drugs of the Future*, 11, 26 (1986).
Moncoda, et al., *Nature*, 263, 663 (1976).
Nickolson, et al., *Med. Res. Rev.*, 5, 1 (1985).
Seiler, et al., *J. Pharmacol. Exp. Ther.*, 255: 1021 (1990).
T. Shioiri, Y. Hamada, *Heterocycles*, 27: 1035: (1988).
Wasserman, et al., *Chem. Rev.*, 86: 845 (1986).
G. D. Hartman, L. M. Weinstock, *Org. Syn.*, VI, 620 (1988).
J. L. Kraus, *Synth. Comm.*, 16:827 (1986).
J. F. W. McOmie, M. L. Watts, *Chem. Ind.*, 1658 (1963).
Negishi et al., *J. Org. Chem.*, 42: 1821 (1977).
Wasserman, et al., *Tetrahedron Lett.*, 22: 1737 (1981).
R. F. Abdulla, R. S. Brinkmeyer, *Tetrahedron*, 35: 1675 (1979).
A. P. Kozikowski, A. J. Ames, *J. Org. Chem.*, 45: 2548 (1980).
Moriya, et al., *J. Med. Chem.*, 29: 333 (1986).
D. Hoppe, *Angew. Chem., Int. Ed.*, 13:789 (1974).
J. Frump, *Chem. Rev.*, 71:483 (1971).
H. Eckert, B. Forster, *Angew. Chem., Int. Ed.*, 26:894 (1987).
Suzuki, et al., *J. Org. Chem.*, 38:3571–3575 (1973).
H. Reimlinger, *Chemistry and Industry*, 1082–1083 (1970).
Davidson, et al., *J. Org. Chem.*, 2:319 (1937).
I. Yamawaki, K. Ogawa, *Chem. Pharm. Bull.*, 36:3142 (1988).
Meanwell, et al., *J. of Med. Chem.*, 35:389–397 (1992).
Merritt, et al., *Br. J. Pharmacol.*, 102:260–266 (1991).
Merritt, et al., *Br. J. Pharmacol.*, 102:251–259 (1991).

DIPHENYLOXAZOLYL-OXAZOLES AS PLATELET AGGREGATION INHIBITORS

BACKGROUND OF THE INVENTION

1. Field of the Invention

This invention relates to a series of novel oxazole derivatives which are useful as inhibitors of ADP-induced aggregation of human blood platelets in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, *J. Atherosclerosis Research*, 8: 721 (1968)).

Octimibate (1) is a broad spectrum inhibitor of platelet aggregation; $IC_{50}=1$ µg/ml (human PRP vs ADP). (a. U.S. Pat. No. 4,460,598 b. Lautenschlager, et al., *Drugs of the Future*, 11, 26 (1986)).

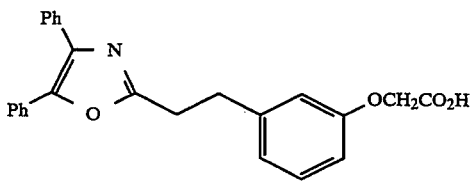

(1)

EPO 0434034, to Meanwell, et al., discloses (2), which is an orally active broad spectrum inhibitor of platelet aggregation.

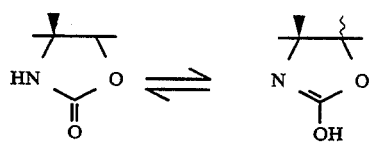

(2)

SUMMARY OF THE INVENTION

The present invention provides novel oxazole derivatives having Formual I, infra. or pharmaceutically acceptable salt thereof, which have enhanced potency and aqueous activity.

The compounds of Formula I are useful as inhibitors of adenosine diphosphate-induced aggregation of human blood platelets in platelet rich plasma.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

DETAILED DESCRIPTION OF THE INVENTION

The compounds of the instant invention comprise those of Formula I

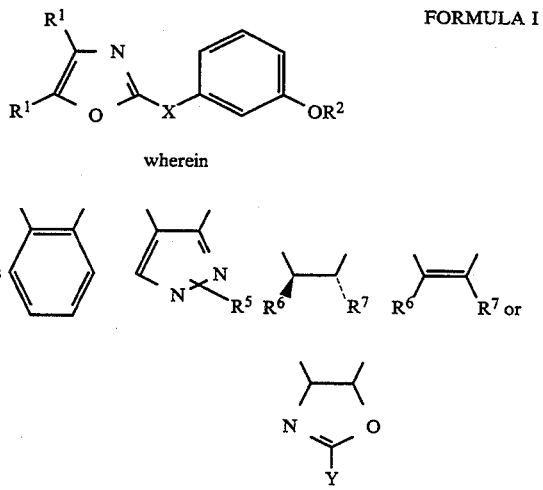

FORMULA I wherein

X is

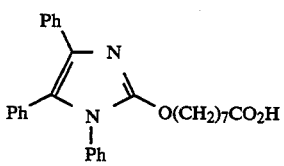

Y is $CH_3$, Ph, or OH, provided that when Y is OH, the compound exists in the keto-enol tautaumerism form $R^1$ is Ph or Th;
$R^2$ is H or $CH_2R^3$;
$R^3$ is H, $OCH_3$, $C_1$–$C_5$ lower alkyl, or $CO_2R^4$;
$R^4$ is H or $C_1$–$C_5$ lower alkyl;
$R^5$ is H or $CH_3$;
$R^6$ is OHCHN or $H_2N$; and
$R^7$ is H or OH;
or pharmaceutically acceptable salt thereof.

It is understood that as used herein limitations of Formula I are defined as follows:

The term "$C_1$–$C_5$ lower alkyl" refers to a branched or unbranched saturated hydrocarbon chain containing from 1 to 5 carbon atoms, for example, methyl, ethyl, n-propyl, isopropyl, butyl, isobutyl, and 3-pentyl.

The symbol "Ph" represents phenyl. The symbol "Th" represents thiophene.

According to the present invention, the compounds characterized by Formula I and the pharmaceutically acceptable acid addition salts thereof, were prepared as outlined in Schemes I–VI.

As shown in Scheme I, attack of benzoin on methyl oxalyl chloride prior to reflux in ammonium acetate/acetic acid solution delivered the methyl ester (1). Isonitrile (2), obtained by formulation and dehydration of 3-methoxybenzylamine, was treated with s-butyllithium followed by dropwise addition of 1 and gave the oxazole (3). The side chain was appended after deprotection to the phenol with boron tribromide. (J. F. W. McOmie, M. L. Watts, *Chem. Ind.*, 1658 (1963). Alkylation with methyl bromoacetate gave 4, which was hydrolyzed in lithium hydroxide solution to 5.

alyzed cross coupling with 3-hydroxyiodobenzene derivative (9) to give 10. (E.-I. Negishi, A. O. King, N. Okukado, *J. Org. Chem.*, 42, 1821 (1977). Deprotection, alkylation, and hydrolysis as above gave compounds 6 and 7.

SCHEME I

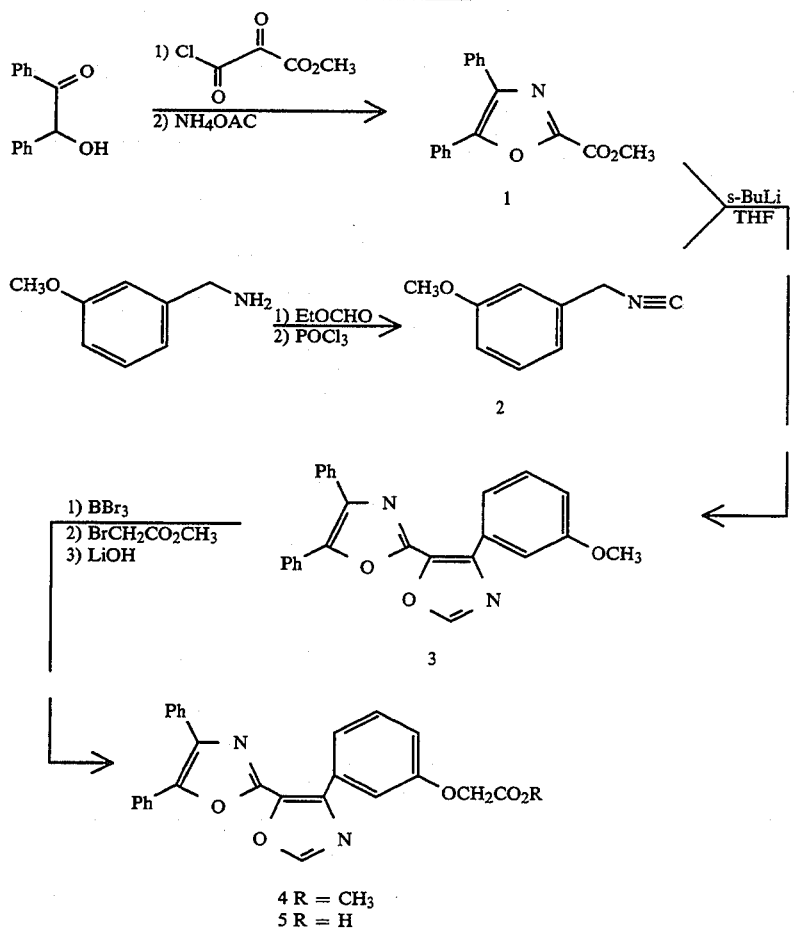

Replacement of the central heterocyclic ring by a benzene nucleus yielded products 6 and 7 (Scheme II). The aromatic bromide (8), prepared from benzoin and 2-bromobenzoic acid, was subjected to palladium-cat-

SCHEME II

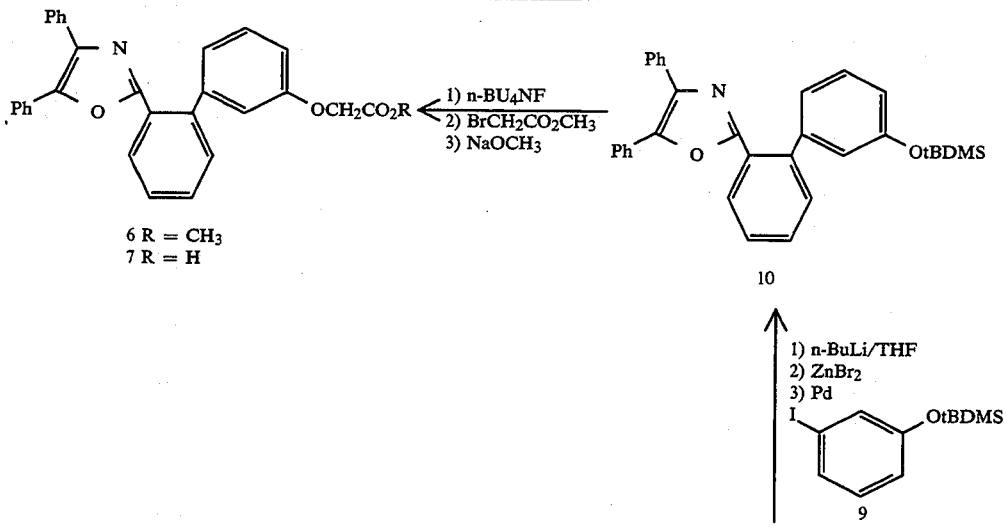

-continued
SCHEME II

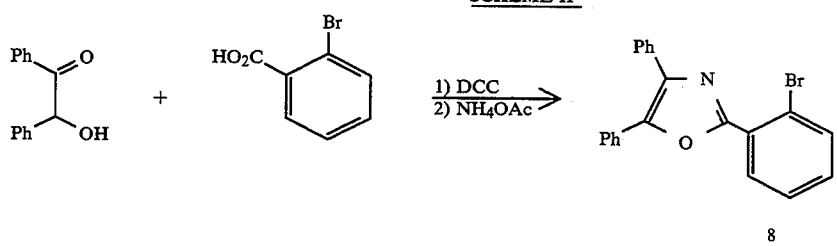

The pyrazoles (11) through (16) (Scheme III) were prepared from 2-methyl-4,5-diphenyloxazole (17). (H. H. Wasserman, R. J. Gambale, M. J. Pulmer, *Tetrahedron Lett.*, 22, 1737 (1981). Acylation with benzoic ester (18) provided ketone (19), which upon heating in the presence of N,N-dimethylformamide dimethyl acetal formed enamide (20). Addition of methyl hydrazine supplied the substituted pyrazoles (21) and (22), (R. F. Abdulla, R. S. Brinkmeyer, *Tetrahedron*, 35, 1675 (1979)) which were separated by chromatography. Subsequent treatment with fluoride ion, alkylation with methyl bromoacetate, and hydrolysis gave products 11 through 14.

Compound 20 was deblocked and alkylated with t-butyl bromoacetate followed by reaction with hydrazine under carefully controlled conditions. Deesterification (trifluoroacetic acid) and reesterification (methanol/sulfuric acid) lead to pyrazoles (15) and (16).

SCHEME III

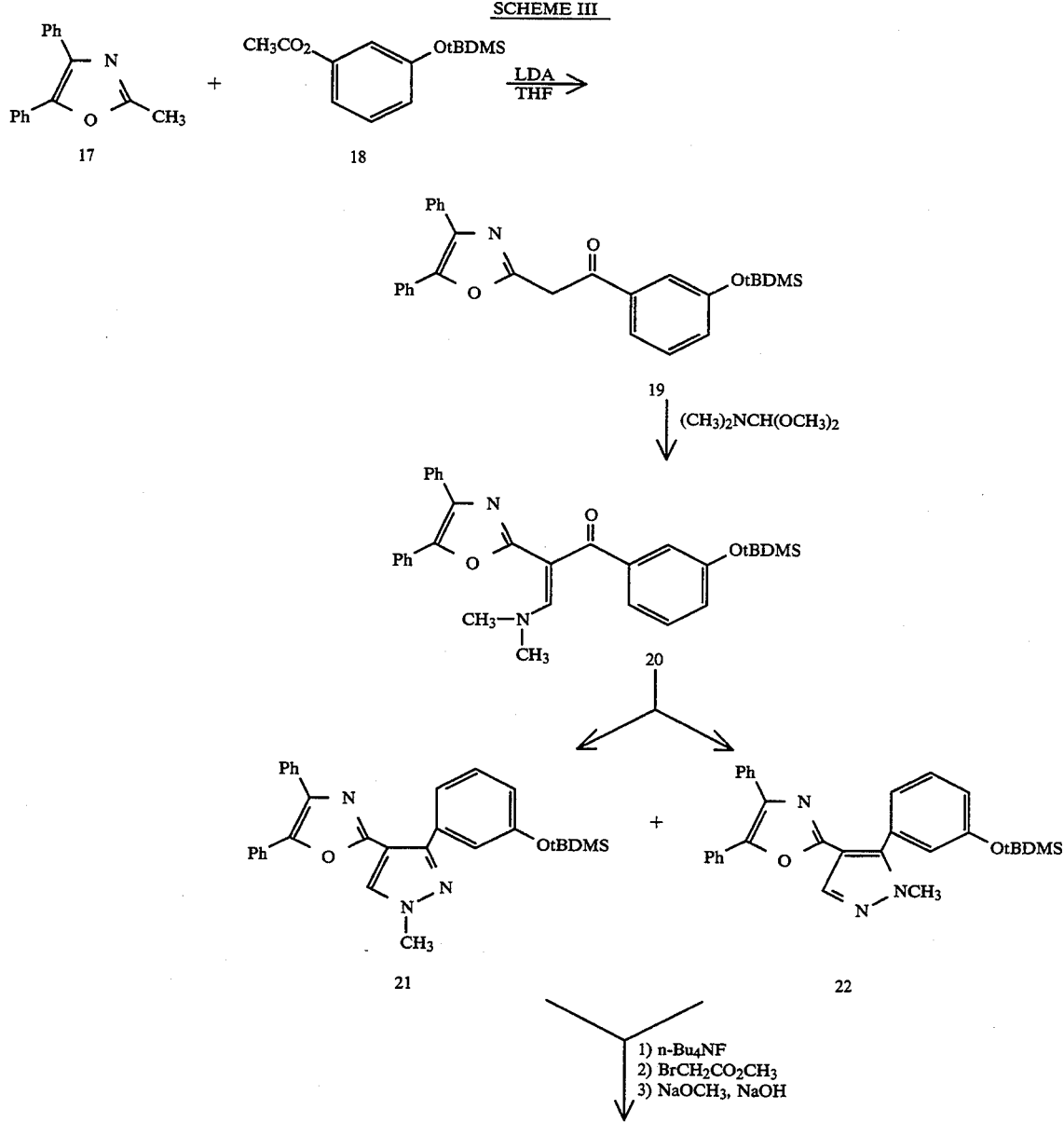

-continued
SCHEME III

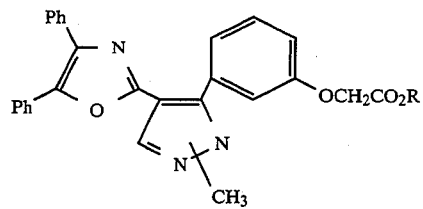

11 (R = CH₃, 3-me)
12 (R = H, 3-me)
13 (R = CH₃, 5-me)
14 (R = H, 5-me)

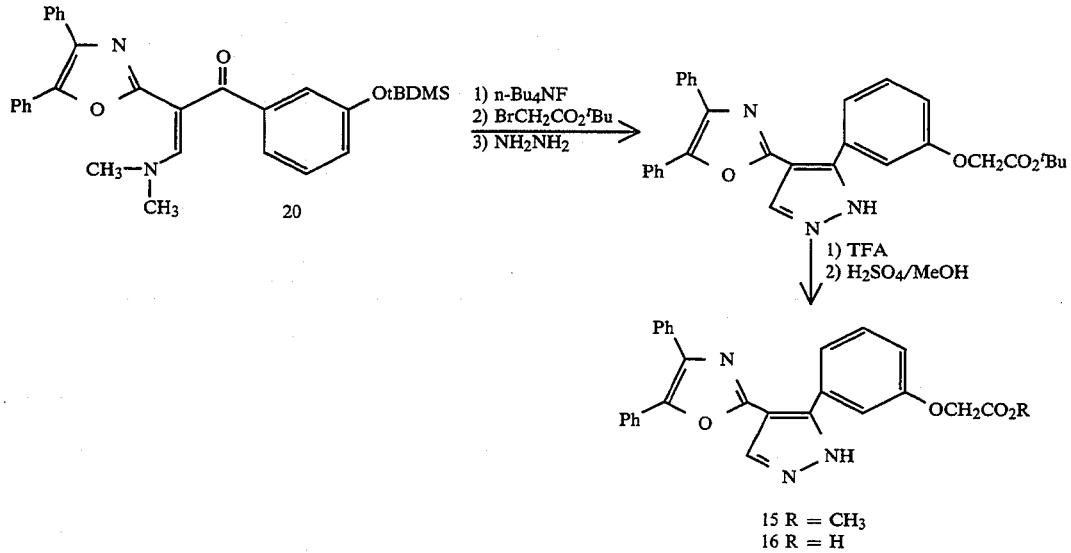

15 R = CH₃
16 R = H

Compounds 23–26 were synthesized as depicted in Scheme IV. Accordingly, isonitrile (27) was condensed with 3-methoxybenzoic acid to provide 28. Deprotonation with s-butyllithium and quench of the resultant anion with methyl iodide furnished 29. (A. P. Kozikowski, A. J. Ames, *J. Org. Chem.*, 45, 2548 (1980)). Alternatively, hydrolysis of 28 liberated an amino ketone, which was acylated with benzoyl chloride and recyclized to formulate the 2-phenyl derivative (30). (T. Moriya, S. Takabe, S. Maeda, K. Matsumoto, K. Takashima, T. Mori, S. Takeyama, *J. Med. Chem.*, 29, 333 (1986)). Both intermediates were readily converted to products 23–26.

SCHEME IV

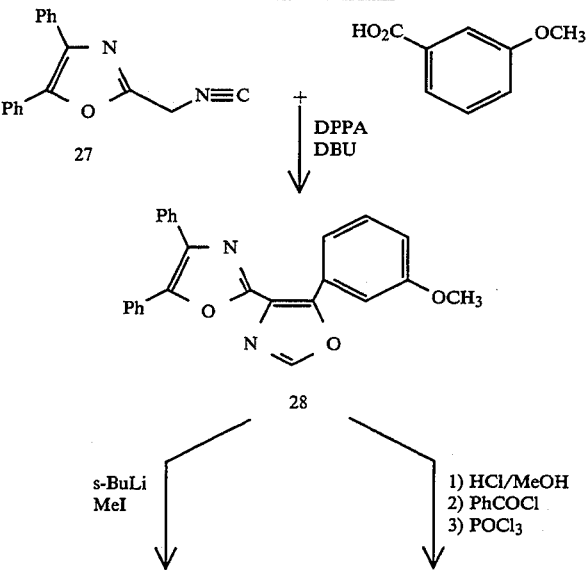

SCHEME IV -continued

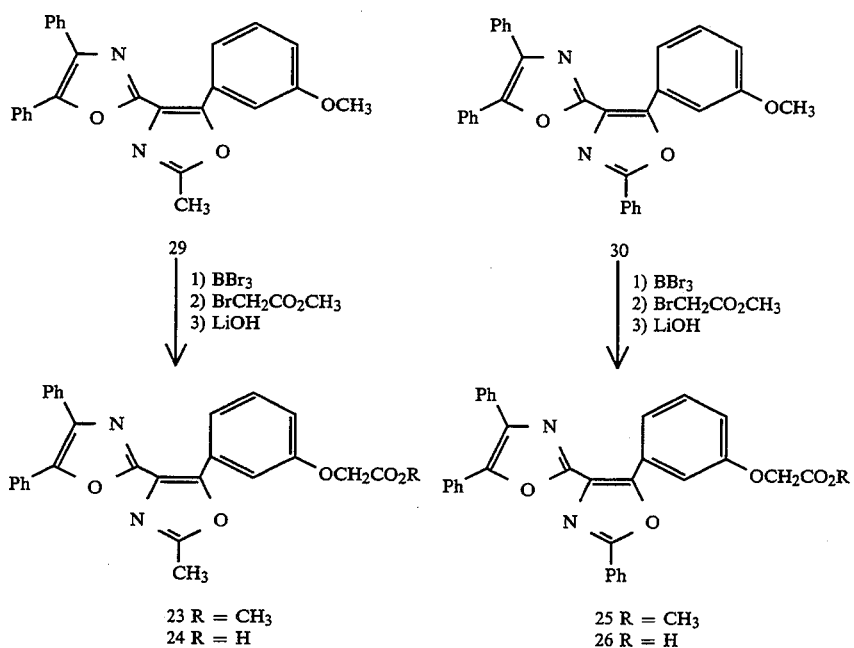

23 R = CH₃
24 R = H

25 R = CH₃
26 R = H

Condensation of 27 with methyl(3-formylphenoxy)acetate and quench with ammonium chloride solution yielded a 4:1 mixture of 31 and 32, respectively. (D. Hoppe, *Angew. Chem., Int. Ed.,* 1974, 13, 789 (1974)) (Scheme V). The formamide (32) was produced upon hydrolysis of the less stable cis oxazoline. Quench of the reaction with dilute acid lead directly to the mixture of cis and trans formamides (32) and (33). Additionally, quenching the same reaction with water gave a mixture of trans and cis olefins (34) and (35). Basic hydrolysis of 31 cleaved the methyl ester, however, the oxazoline ring did not survive acidic work up and the formylamino alcohol (36) was obtained. (Scheme V). Hydrolysis of 33 gave 37, and reesterfication of 37 delivered methyl ester (38) (Scheme VI).

As shown in Scheme VI, the cis and trans substituted oxazolines and oxazolidinones (39–45) (J. Frump, *Chem. Rev.,* 71, 483 (1971), H. Eckert, B. Forster, *Angew. Chem., Int. Ed.,* 26, 894 (1987)) were synthesized by carrying through the formamide mixture (32 and 33) to methyl ester stage (38). Condensation with trimethylorthoacetate and orthobenzoate yielded the corresponding cis and trans substituted oxazolines. The oxazolidinones (43–45) (Scheme VI) were generated upon treatment of cis and trans 38 with triphosgene and hydrolysis of the methyl ester.

SCHEME V

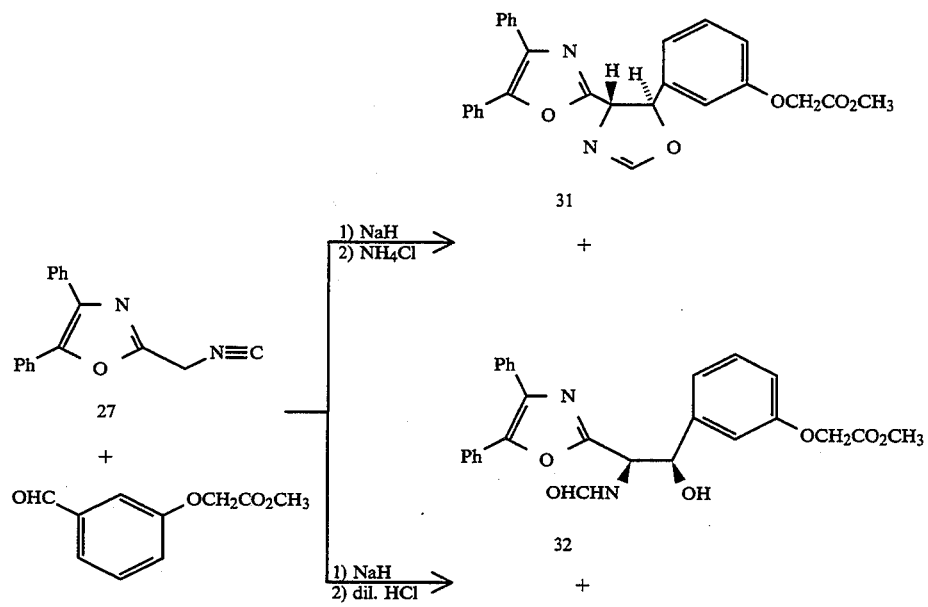

-continued
SCHEME V
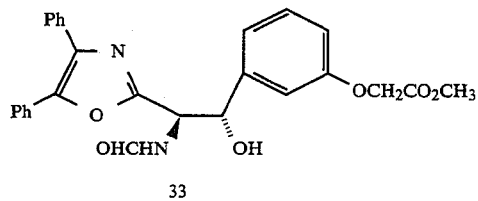
33
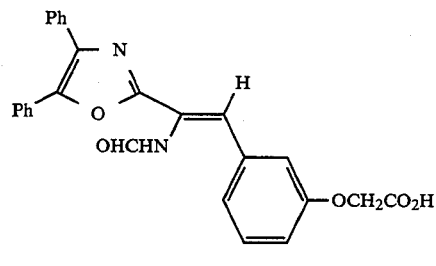
34
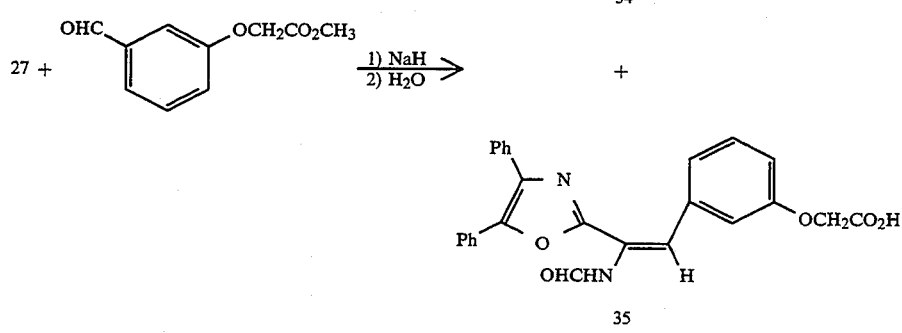
35
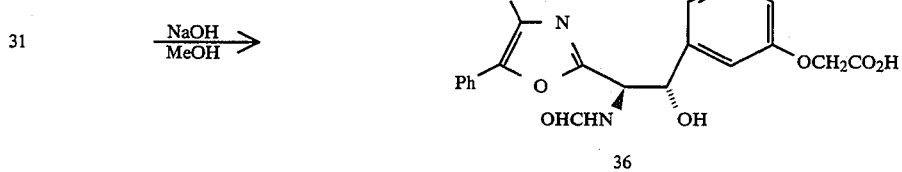
36
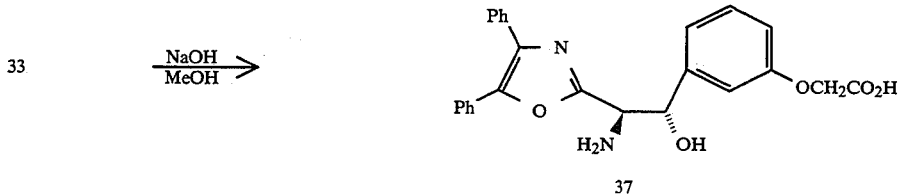
37
SCHEME VI
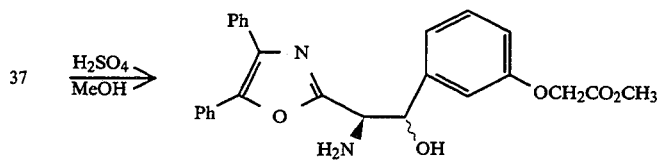
38

SCHEME VI -continued

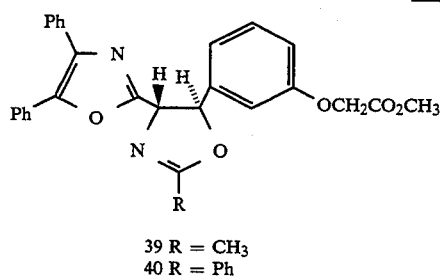

39 R = CH₃
40 R = Ph

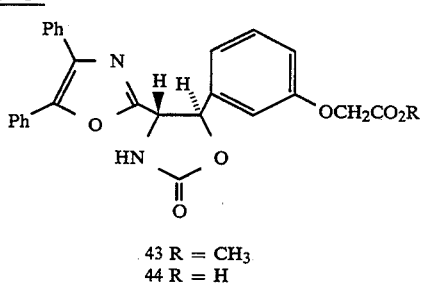

43 R = CH₃
44 R = H

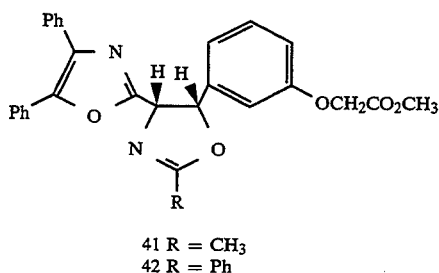

41 R = CH₃
42 R = Ph

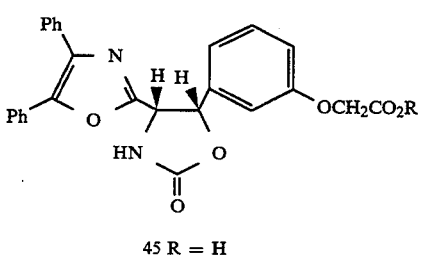

45 R = H

In Vitro Inhibition of Human Platelet Aggregation

The aggregometer method of Born, G. V. R., *J. Physiol.*, (London), 162, 67–68, (1962) as modified by Mustard, J. F., et al., *J. Lab. Clin. Med.*, 64, 548–599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140×g) from citrated (3.8%) human blood. All glassware used for preparation of PRP is silicon treated. ADP in final concentration of 0.5 mcg/mL or 0.05 mL of a collagen suspension prepared according to the method described by Evans, G., et al., *J. Exp. Med.*, 128, 877–894, (1968) was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 mcg/ml vs. ADP and 245 mcg/ml vs collagen. Results for 50% inhibition of ADP-induced aggregation are given hereinafter.

The target compounds were evaluated as inhibitors of ADP-induced aggregation of human blood platelet in platelet-rich-plasma (PRP) in vitro. The test compounds were incubated at about 37° C. in PRP for about 3 minutes prior to the addition of sufficient ADP to provide final ADP concentration of 5.86 mM.

TABLE 1

| Compound | $IC_{50}$ μg/ml (human PRP vs ADP) |
|---|---|
| 4 | 0.174 |
| 5 | 0.07 |
| 6 | 32 (34%) |
| 7 | 5 |
| 11 | 1.12 |
| 12 | 0.30 |
| 13 | 0.75 |
| 14 | 0.50 |
| 15 | 0.07 |
| 16 | 0.08 |
| 23 | 0.13 |
| 24 | 0.02 |
| 25 | 32 (6%) |
| 26 | 32 |
| 31 | 0.08 |
| 39 | 0.65 |
| 40 | 10 |
| 41 | 27 |
| 42 | 32 (15%) |
| 43 | 5 |
| 44 | 1 |
| 45 | 32 (8%) |
| 33 | 10 |
| 36 | 6.5 |
| 38 | 2.8 |
| 37 | 0.9 |

The Formula I compounds or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient. Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

Methyl 4,5-diphenyl-2-oxazolecarboxylate, (1)

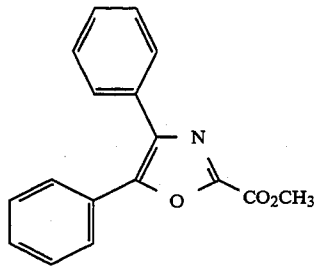

Benzoin (25 g, 118 mmol) was dissolved in THF (500 mL) and triethylamine (27 mL) under $N_2$. Chloro methyl glyoxylate (11 mL, 120 mmol) was added dropwise and the reaction mixture stirred about 45 minutes before being filtered and concentrated. The residue was suspended in a solution of ammonium acetate (45 g, 0.6 mol) in (500 mL) acetic acid, heated at reflux for about 6 hours, diluted with water ($\frac{1}{2}$ vol) and extracted with dichloromethane. The organic layers were washed with $NaHCO_3$ solution, brine, and dried ($MgSO_4$). Concentration onto $SiO_2$ and gradient chromatography (elution; 10% to 40% ethyl acetate/hexanes) followed by recrystallization from diethyl ether/chloroform gave (1) 6.5 g (20%), mp 114°–116° C. IR (KBr, cm$^{-1}$) 3032, 3004, 2952, 1742, 1540, 1478, 1438, 1326, 1212, 1140, 776, 698. $^1$H NMR (300 MHz, CDCl$_3$) δ 4.04 (3H, s), 7.30 to 7.42 (6H, m), 7.63 to 7.71 (4H, m). $^{13}$C NMR (75 MHz, CDCl$_3$) ppm 53.48, 127.42, 127.77, 128.43, 128.86, 129.05, 130.03, 131.32, 137.66, 149.03, 150.70, 156.47. m/e 280 (MH+).

Anal. Calcd. for $C_{17}H_{13}N_1O_3$: C, 73.11; H, 4.69; N, 5.01. Found: C, 72.82; H, 4.68; N, 5.09.

EXAMPLE 2

2-(2-Bromophenyl)-4,5-diphenyloxazole, (8)

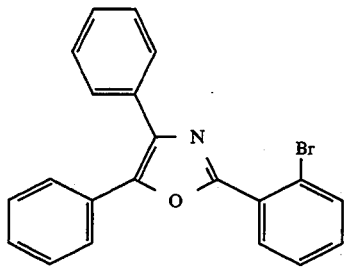

A mixture of benzoin (20 g, 94.2 mmol), 2-bromobenzoic acid (21.8 g, 108 mmol), 1,3-dicyclohexylcarbodiimide (24.3 g, 118 mmol), and DMAP (cat.) were suspended in dichloromethane (200 mL) and stirred about 1.5 hours under $N_2$. The reaction mixture was filtered, concentrated, and the residue dissolved in ammonium acetate (36 g, 471 mmol)/acetic acid (350 mL) solution, and heated at reflux for about 1.5 hours. After being cooled, the solution was poured onto ethyl acetate/water (1 vol), and the organic phase washed with water, brine, and dried (MgSO$_4$). Chromatography (elution with 12% ethyl acetate/hexanes) gave (8) 33.64 g (95%). IR (KBr, cm$^{-1}$) 3070, 3060, 1750, 1605, 1585, 1565, 1525, 1505, 1480, 1450, 1445, 1430, 1370, 1335, 1230, 1028, 970, 765, 730, 700, 690. $^1$H NMR (300 MHz, CDCl$_3$) δ 7.2 to 7.45 (8H,m), 7.65 to 7.8 (5H,m), 8.05 to 8.15 (1H,m). m/e 376 (MH+).

EXAMPLE 3

2'-(4, 5-Diphenyl-2-oxazolyl)-[1,1'-biphenyl-3-ol]

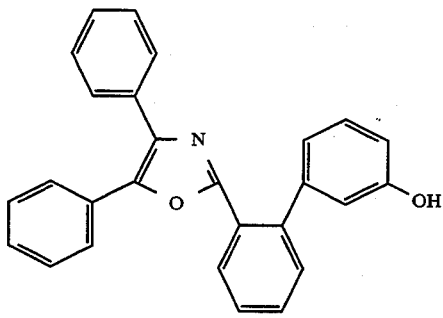

n-Butyllithium (3.7 mL of 2.5M in hexanes) was added dropwise to 2-(2-bromophenyl)-4,5-diphenyloxazole (8) (3 g, 7.98 mmol) in THF (40 mL) under N$_2$ at about −78° C., and the solution stirred about 15 minutes before zinc bromide (2.07 g, 9.18 mmol) dissolved in 15 mL of the same solvent was added. After about 30 minutes, a THF solution (4 mL) of (1,1-dimethylethyl)(3-iodophenoxy)dimethylsilane (9) (2.67 g, 7.98 mmol) was added followed by (460 mg, 0.4 mol) of tetrakis (triphenyl-phosphine)palladium (0) in THF (20 mL). The reaction mixture was stirred about 17 hours, poured onto ether/ammonium chloride solution, and the organic layer was washed with brine and dried (MgSO$_4$). Purification by flash column chromatography (elution with 5% ethyl acetate/hexanes) gave (25) 3.2 g (80%). The material was taken up in THF (70 mL) and 9.3 mL of tetra-n-butylammonium fluoride solution (1M in THF, 9.33 mol) added dropwise. The reaction mixture was stirred about 1 hour, poured onto ether/ammonium chloride solution (1 vol), and the organic phase washed with water and brine before drying (MgSO$_4$). Chromatography (elution with 15% ethyl acetate/hexanes) gave the phenol 1.92 g (79%) as a white foam, which was recrystallization from ether/hexanes to white needles, mp 125°–128° C. IR (KBr, cm$^{-1}$) 3380, 3060, 1595, 1455, 1445, 1305, 1210, 965, 755, 695. $^1$H NMR (300 MHz, CDCl$_3$) δ 6.52 (1H, t, 2.0 Hz), 6.86 to 6.88 (2H, m), 7.03 to 7.06 (2H, m), 7.19 to 7.50 (12H, m), 7.89 (1H, Br.s), 8.02 to 8.05 (1H, m). $^{13}$C NMR (75 MH$_3$, CDCl$_3$) ppm 114.38, 115.53, 120.45, 125.39, 126.18, 127.56, 127.98, 128.14, 128.40, 128.47, 129.36, 129.75, 130.23, 130.66, 131.66, 135.45, 141.48, 142.65, 145.65, 145.80, 156.15, 160.98. m/e 390 (MH+).

Anal. Calcd. for C$_{27}$H$_{19}$N$_1$O$_2$.0.2H$_2$O: C, 82.51; H, 4.98; N, 3.57; H$_2$O, 0.92%. Found: C, 82.28; H, 4.99; N, 3.47; H$_2$O, 0.64%.

EXAMPLE 4

Methyl[2'-(4,5-diphenyl-2-oxazolyl)-[1,1'-biphenyl]-3-yloxy]acetate, (6)

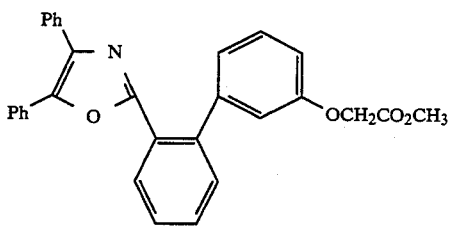

A mixture of 2'-(4,5-diphenyl-2-oxazolyl)-[1,1'-biphenyl-3-ol] (1.18 g, 3.03 mmol), methyl bromoacetate (0.32 mL, 3.3 mmol), potassium carbonate (500 mg, 3.6 mmol), and potassium iodide (cat.), was heated at reflux in acetonitrile (60 mL) for about 5 hours. After being cooled to room temperature, the solution was filtered and concentrated. Chromatography (elution with 15% ethyl acetate/hexanes) gave (6) 1.19 g (86%) as clear colorless resin. IR (film, cm$^{-1}$) 3060, 3025, 2950, 1760, 1605, 1575, 1315, 1195, 1085, 962, 755, 695. $^1$H NMR (300 MH, CDCl$_3$) δ 3.65 (3H, s), 4.56 (2H, s), 6.90 to 6.98 (3H, m), 7.08 to 7.11 (2H, m), 7.17 to 7.20 (3H, m), 7.28 to 7.40 (5H, m), 7.45 to 7.48 (2H, m), 7.63 to 7.67 (2H, m), 8.13 to 8.19 (1H, m). $^{13}$C NMR (75 MHz, CDCl$_3$) ppm 52.17, 65.51, 113.70, 115.22, 122.68, 126.11, 126.15, 127.77, 128.10, 128.16, 128.32, 128.43, 128.54, 128.69, 129.27, 129.76, 130.07, 130.85, 132.56, 136.03, 141.01, 143.47, 145.66, 157.77, 160.36, 169.25. m/e 462 (MH+).

Anal. Calcd. for C$_{30}$H$_{23}$N$_1$O$_4$.0.1 H$_2$O: C, 77.78; H, 5.05; N, 3.03; H$_2$O, 0.39%. Found: C, 77.29; H, 4.87; N, 2.96; H$_2$O, 0.14%.

EXAMPLE 5

[2'-(4,5-Diphenyl-2-oxazolyl)-[1,1'-biphenyl]-3-yloxy]acetic acid, (7)

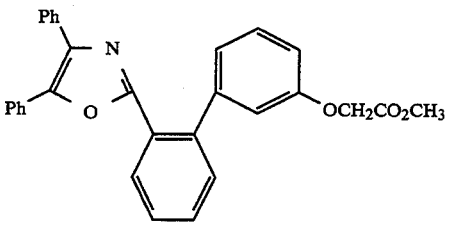

Methyl[2'-(4,5-diphenyl-2-oxazolyl)-[1,1'-biphenyl]-3-yloxy]acetate (840 mg, 1.8 mmol) was dissolved in methanol (40 mL), lithium hydroxide monohydrate (150 mg, 3.64 mmol) was added, and the reaction mixture stirred for about 16 hours. The solution was poured onto ethyl acetate/1N HCl solution and the organic layer washed with water and brine before drying (Na$_2$SO$_4$). Concentration and recrystallization (4:1 hexanes/dichloromethane) gave (7) 560 mg (69%) as white crystals, mp 149°–153° C. IR (KBr, cm$^{-1}$) 3440, 3060, 2920, 1745, 1575, 1465, 1180, 1078, 760, 695. $^1$H NMR (300 MHz, CDCl$_3$/ DMSO-d$_6$) δ 4.19 (2H, s), 6.55 to 6.61 (3H, m), 6.72 to 6.75 (2H, m), 6.85 to 6.87 (3H, m), 6.93 to 7.18 (7H, m), 7.24 to 7.29 (2H, m), 7.77 to 7.80 (1H, m). $^{13}$C NMR (75 MHz, CDCl$_3$/DMSO-d$_6$) ppm 65.03, 113.04, 115.18, 121.97, 125.67, 125.78, 127.49, 127.73, 127.95, 128.15, 128.24, 128.28, 128.92, 129.37, 129.93, 130.63, 132.16, 135.60, 140.72, 142.88, 145.26, 157.64, 159.92, 170.35. m/e 448 (MH+).

Anal. Calcd. for C29H21N1O4.0.15 H2O: C, 77.38; H, 4.77; N, 3.12; H2O, 0.60%. Found: C, 77.03; H, 4.97; N, 3.17; H2O, 0.21%.

EXAMPLE 6

1-[3-[(1,1-Dimethylethyl)dimethylsiloxy]phenyl]-2-[(dimethylamino)methylene]-2-(4,5-diphenyl-2-oxazolyl)ethanone

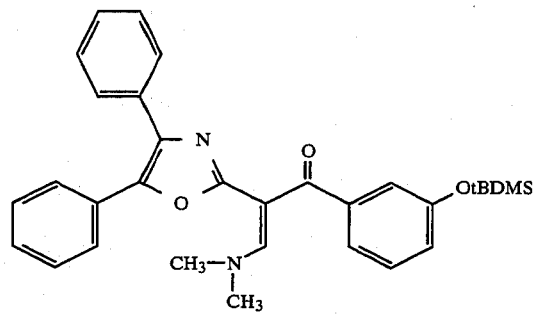

A neat mixture of 1-[3-[(1,1-dimethyl)dimethylsiloxy]phenyl]-2-(4,5-diphenyl-2-oxazolyl)ethanone (19) (15 g, 32.2 mmol) and dimethylformamide dimethyl acetal (43 mL, 0.32 mmol) was heated at reflux for about 45 minutes. Chromatography (elution with 10% diethyl ether/hexanes) gave (20) 11.1 g (65%). IR (KBr, cm$^{-1}$) 2950, 2925, 2855, 1635, 1565, 1550, 1420, 1360, 1295, 940, 895, 835, 760, 695. $^1$H NMR (300 MHz, CDCl3/DMSO-d6) δ 0.08 (6H, s), 0.89 (9H, s), 2.8 to 3.1 (6H, Series of Br. s) 6.79 to 6.83 (1H, m) 7.00 (1H, Br.s), 7.06 to 7.43 (10H, m), 7.60 to 7.65 (2H, m), 7.72 (1H, s). m/e 525 (MH+).

Anal. Calcd. for C32H36N2O3Si: C, 73.25; H, 6.92; N, 5.33%. Found: C, 73.37; H, 6.87; N, 5.27.

EXAMPLE 7

3-[4-(4,5-Diphenyl-2-oxazolyl)-1-methylpyrazolyl]-phenol

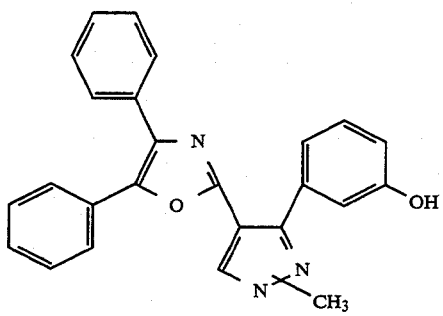

N-Methyl hydrazine (2.5 mL, 46.6 mmol) was added dropwise to 1-[3-[(1,1-dimethylethyl)dimethylsiloxy]-phenyl]-2-[(dimethylamino) methylene]-2-(4,5-diphenyl-2-oxazolyl)ethanone (20) (12 g, 22.8 mmol) and the mixture stirred for about 1 hour, diluted with water, and extracted with dichloromethane. The organic phase was concentrated, and the residue was taken up in THF (150 mL), and tetra-n-butylammonium fluoride (27.84 mL of 1M solution) added. The reaction mixture was stirred about 5 minutes, concentrated, diluted with 1N HCl, and extracted with dichloromethane. Separation by SiO2 chromatography, (elution with 75% ether/hexanes) and recyrstallization from dichloromethane/ether/hexanes gave 3-methyl 2.3 g, (25%), mp 186°–188° C. and 5-methyl 2.85 g (50%), mp 213°–215° C. both as white solids.

3-methyl: IR (KBr, cm$^{-1}$) 3270, 1605, 1590, 1525, 1445, 1180, 965, 875, 765, 740, 695. $^1$H NMR (300 MHz, CDCl3) δ 3.90 (3H, s) 6.81 to 6.84 (1H, m), 7.21 to 7.35 (10H, m), 7.41 to 7.45 (2H, m), 7.60 to 7.64 (2H, m), 8.04 (1H, s). $^{13}$C-NMR (75 MHz, CDCl3) ppm 39.20, 108.36. 115.76, 116.27, 121.15, 126.02, 128.12, 128.24, 128.56, 128.59, 128.67, 129.21, 132.28, 132.66, 133.56, 144.16, 150.32, 155.74, 155.91. m/e 394 (MH+).

Anal. Calcd. for C25H19N3O2.0.1 H2O: C, 75.98; H, 4.91; N, 10.64, H2O, 0.46%. Found: C, 75.83; H, 4.91; N, 10.54; H2O, 0.25%.

5-methyl: IR (KBr, cm$^{-1}$) 3430, 3060, 1615, 1585, 1480, 1445, 1285, 1235, 1195, 1065, 960, 875, 795, 765, 740, 690. $^1$H NMR (300 MHz, CDCl3) δ 3.70 (3H,s), 6.76 (1H, Br. s), 6.92 to 6.99 (2H, m), 7.23 to 7.36 (9H, m), 7.57 to 7.61 (2H, m), 7.75 (1H, Br. s), 8.18 (1H, s). $^{13}$C NMR (75 MHz, CDCl3) ppm 37.29, 109.21, 116.76, 117.11, 121.82, 125.77, 128.18, 128.28, 128.52, 128.59, 129.72, 129.97, 132.16, 135.56, 138.57, 142.58, 144.30, 155.90, 156.51. m/e 394 (MH+).

Anal. Calcd. for C25H19N3O2.0.2 H2O: C, 75.63; H, 4.93; N, 10.59, H2O, 0.91%. Found: C, 75.70; H, 4.88; N, 10.44; H2O, 0.20%.

EXAMPLE 8

Methyl[3-[4-(4,5-diphenyl-2-oxazoly)-1-methyl-3-pyrazolyl]phenoxy]acetate, (11)

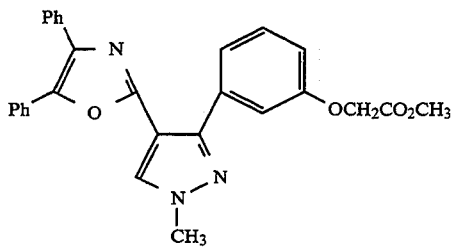

A mixture of 3-[4-(4,5-diphenyl-2-oxazolyl)-1-methyl-3-pyrazolyl]phenol (2.85 g, 7.25 mmol), methyl bromoacetate (0.70 mL, 7.61 mmol), and potassium carbonate (1.2 g, 8.70 mmol), was heated at reflux in acetonitrile (50 mL) for about 30 minutes. After being cooled to room temperature, the solution was filtered and concentrated to give (11) 2.37 g (70%) as an oil. Recrystallization from ethanol gave an amorphous solid mp 121°–123°. IR (KBr, cm$^{-1}$) 3440, 3060, 2945, 1765, 1605, 1580, 1435, 1210, 1165, 1075, 1060, 965, 765, 735, 695. $^1$H NMR (300 MHz, CDCl3) δ 3.78 (3H, s) 4.68 (3H, s), 7.02 to 7.04 (1H, m), 7.28 to 7.42 (8H, m), 7.52 to 7.60 (3H, m), 8.11 (1H, m). $^{13}$C-NMR (75 MHz, CDCl3) ppm 39.38, 52.15. 65.50, 108.67, 115.05, 115.37, 122.42, 126.23, 128.10, 128.29, 128.57, 128.61, 128.86, 129.18, 132.65, 134.10, 155.64, 157.55, 169.36. m/e 466 (MH+).

Anal. Calcd. for C28H23N3O4: C, 72.25; H, 4.98; N, 9.03. Found: C, 71.95; H, 4.95; N, 8.88.

EXAMPLE 9

Methyl[3-[4-(4,5-diphenyl-2-oxazolyl)-1-methyl-5-pyrazolyl]phenoxy]acetate, (13)

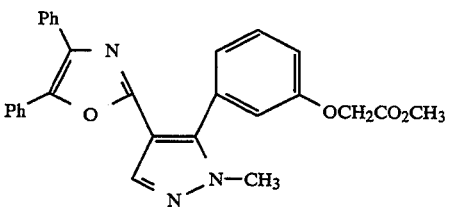

A mixture of 3-[4-(4,5-diphenyl-2-oxazolyl)-1-methyl-5-pyrazolyl]phenol (2.0 g, 5.09 mmol), methyl bromoacetate (0.50 mL, 5.34 mmol), and potassium carbonate (842 mg, 6.1 mmol), was heated at reflux in acetonitrile (35 mL) for about 25 minutes. After being cooled to room temperature, the solution was filtered and concentrated to give (13) 2.1 g (88%) as an oil. Recrystallization from ethanol gave an amorphous solid, mp 137°–138° C. IR (KBr, cm$^{-1}$) 3060, 2950, 2910, 1765, 1625, 1605, 1590, 1430, 1205, 865, 765, 745, 695. $^1$H NMR (300 MHz, CDCl$_3$) δ 7.07 to 7.16 (3H, m), 7.21 to 7.35 (9H, m), 7.45 (1H, t, J=7.8 Hz), 7.60 to 7.65 (2H, m), 8.16 (1H, s). $^{13}$C-NMR (75 MHz, CDCl$_3$) ppm 37.51, 52.27, 65.46, 109.80, 115.80, 116.79, 123.71, 125.83, 128.05, 128.16, 128.47, 128.54, 128.88, 129.69, 130.65, 132.66, 135.87, 138.58, 157.78, 169.05. m/e 466 (MH+).

Anal. Calcd. for C$_{28}$H$_{23}$N$_3$O$_4$: C, 72.24; H, 4.98; N, 9.03. Found: C, 72.22; H, 4.96; N, 8.90.

EXAMPLE 10

3-[4-(4,5-Diphenyl-2-oxazolyl)-1-methyl-3-pyrazolyl]phenoxy]acetic acid, (12)

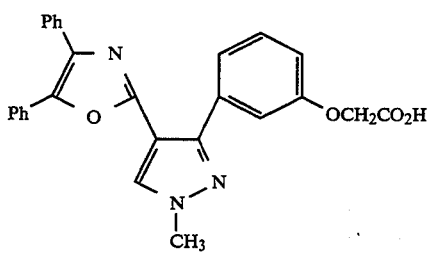

Methyl[3-[4-(4,5-diphenyl-2-oxazolyl)-1-methyl-3-pyrazolyl]phenoxy]acetate (2.0 g, 43 mmol) was dissolved in methanol (30 mL) and 5M NaOH solution (2.6 mL) added. The reaction mixture was heated at reflux for about 15 minutes, concentrated to remove solvent, diluted with water and acidified with 2N HCl solution (pH=1). Extraction into dichloromethane and concentration of the organic phase gave (12) 1.33 g (68%) as a white solid, mp 206°–208° C. IR (KBr, cm$^{-1}$) 3440, 3040, 2930, 2490, 1935, 1730, 1605, 1580, 1205, 1185, 1165, 960, 765, 745, 690. $_1$H NMR (300 MHz, CDCl$_3$) δ 4.00 (3H, s), 4.73 (2H, s), 6.97 to 7.00 (1H, m), 7.37 to 7.66 (13H, m), 8.57 (1H, m), 8.57 (1H, m), 13.02 (1H, Br.s). $^{13}$C-NMR (75 MH$_3$, DMSO-d$_6$) ppm 64.61, 107.11, 114.18, 114.95, 121.42, 126.22, 127.60, 128.27, 128.36, 128.75, 128.81, 128.97, 129.06, 123.03, 133.81, 134.12, 135.24, 143.83, 148.35, 155.05, 157.48, 170.18 m/e 452 (MH+).

Anal. Calcd. for C$_{27}$H$_{21}$N$_3$O$_4$.0.4 H$_2$O: C, 70.71; H, 4.80; N, 9.17 H$_2$O, 1.57%. Found: C, 70.74; H, 4.64; N, 9.05; H$_2$O, 0.29%.

EXAMPLE 11

3-[4-(4,5-Diphenyl-2-oxazolyl)-1-methyl-5-pyrazolyl]-phenoxy]acetic acid,

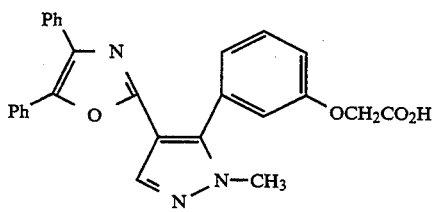

Methyl[3-[4-(4,5-diphenyl-2-oxazolyl)-1-methyl-5-pyrazolyl]phenoxy]acetate (1.7 g, 3.65 mmol) was dissolved in methanol (30 mL) and 5M NaOH solution (2.9 mL) added. The reaction mixture heated at reflux for about 20 minutes, concentrated to remove solvent, diluted with water and acidified with 2N HCl solution (pH=1). The resultant biege solid was filtered to give (14) 1.2 g (66%), mp 113°–116° C. IR (KBr, cm$^{-1}$) 3480, 3060, 2930, 2560, 1720, 1605, 1440, 1250, 1230, 1205, 1080, 960, 875, 765, 740, 690. $^1$H NMR (300 MHz, DMSO-d$_6$) δ 3.76 (3H, s), 4.74 (2H, s), 7.09 to 7.12 (1H, m), 7.18 to 7.24 (2H, m), 7.28 to 7.56 (11H, m), 8.09 (1H, s). $^{13}$C-NMR (300 MHz, DMSO-d$_6$) ppm 64.75, 108.73, 115.46, 116.71, 123.12, 125.70, 127.78, 128.22, 128.41, 128.60, 128.74, 128.90, 129.60, 129.85, 132.16, 137.83, 141.67, 143.51, 155.38, 157.63, 170.12. m/e 452 (MH+).

Anal. Calcd. for C$_{27}$H$_{21}$N$_3$O$_4$.1.1 H$_2$O: C, 68.81; H, 4.97; N, 8.92 H$_2$O, 4.21%. Found: C, 68.41; H, 4.80; N, 8.79; H$_2$O, 3.27%.

EXAMPLE 12

1-[3-Hydroxyphenyl]-2-[(dimethylamino)methylene]-2-(4,5-diphenyl-2-oxazolyl)ethanone

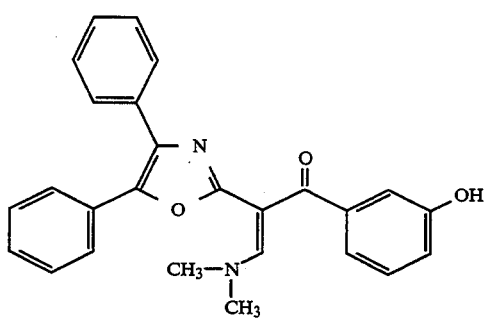

The 1-[3-[(1,1-dimethylethyl)dimethylsiloxy]phenyl]-2-[(dimethylamino)methylene]-2-(4,5-diphenyl-2-oxazolyl)ethanone (19) (10.3 g, 19.6 mmol) was dissolved in THF (100 mL) and tetra-n-butyl ammonium fluoride (17.5 mL of 1M in THF) was added dropwise. The reaction mixture was stirred for about ¼ hour and poured onto an ether (180 mL)/1N HCl(20 mL) solution, and the organic phase separated and dried (MgSO$_4$). Chromatography (elution with 75% ethyl acetate/hexanes) gave the phenol 7.7 g (96%). IR (KBr, cm$^{-1}$) 3170, 3060, 2920, 1735, 1635, 1600, 1447, 1375, 1310, 1210, 1010, 965, 870, 765, 695. $^1$H NMR (300 MHz, CDCl$_3$) δ 2.6 to 3.1 (6H, Series of Br. s) 6.84 (1H, Br.s), 6.95 (1H, Br. s), 7.04 to 7.24 (10H, m), 7.32 to 7.60 (5H, m). m/e 411 (MH+)

Anal. Calcd. for C26H22N2O3.0.5 H2O: C,74.43; H, 5.52; N, 6.67. Found: C,74.10; H, 5.75; N, 6.40.

EXAMPLE 13

1,1-Dimethylethyl-[3-[3-[(dimethylamino)methylene]-2-(4,5-diphenyl-2-oxazolyl)-1-oxo-2-propenyl]phenoxy]acetate

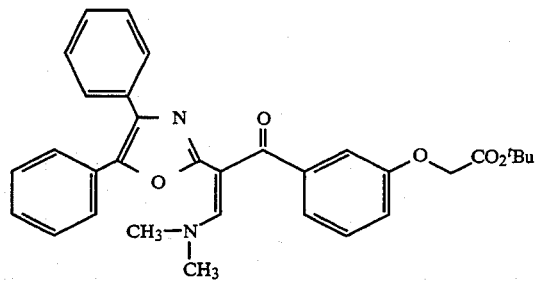

A mixture of 1-[3-hydroxyphenyl]-2-[(dimethylamino)methylene]-2-(4,5-diphenyl-2-oxazolyl)ethanone (3.5 g, 8.75 mmol), t-butyl bromoacetate (1.3 mL, 10.9 mmol), potassium carbonate (1.5 g, 10.9 mmol), and potassium iodide (cat.) was heated at reflux in acetonitrile (75 mL) about for 1 hour. After being cooled to room temperature, the solution was filtered and chromatographed (elution with 5% methanol/dichloromethane) to give product 3.7 g (80.5%). IR (NaCl film, cm$^{-1}$) 2980, 2920, 1750, 1640, 1560, 1425, 1370, 1305, 1225, 1150, 1080, 960, 760, 695. $^1$H NMR (300 MHz, CDCl3) δ 1.42 (9H, s), 2.8 to 3.3 (6H, Series of Br. s) 4.39 (2H, s), 6.95 to 7.38 (12H, m), 7.60 to 7.73 (3H, m). m/e 525 (MH+).

Anal. Calcd. for C32H32N2O5.0.9 H2O: C,71.06; H, 6.30; N, 5.18. Found: C,71.10; H, 6.28; N, 5.04.

EXAMPLE 14

1,1-Dimethylethyl-[3-[4-(4,5-diphenyl-2-oxazolyl)-5-pyrazolyl]phenoxy]acetate

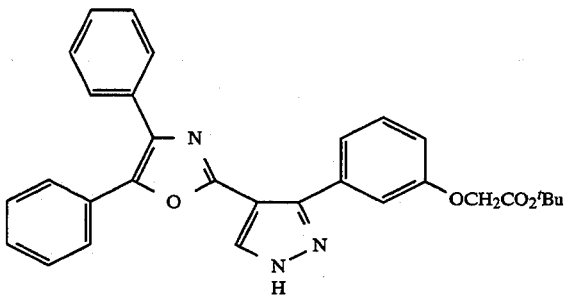

1,1-Dimethylethyl-[3-[3-[(dimethylamino) methylene]-2-(4,5-diphenyl-2-oxazolyl)-1-oxo-2-propenyl]phenoxy]acetate (611 mg, 0.78 mmol) was dissolved in ethanol (abs.) and cooled to about 0° C. Hydrazine (25 mg, 0.8 mmol) was added and the reaction mixture stirred about 1 hour before being warmed to room temperature for about 15 minutes. Concentration and chromatography (elution with 75% ether/hexanes) gave the product 289 mg (75%) as an oil. IR (NaCl film, cm$^{-1}$) 2920, 2840, 1750, 1555, 1535, 1215, 1200, 755. $^1$H NMR (300 MHz, CDCl3) δ 1.44 (9H, s) 4.53 (2H, s), 7.00 to 7.03 (1H, m), 7.25 to 7.57 (11H, m) 7.67 to 7.70 (2H, m), 8.23 (1H, s). m/e 494 (MH+).

Anal. Calcd. for C30H27N3O4: C, 73.00; H, 5.51; N, 8.51. Found: C,72.33; H, 5.39; N, 8.36.

EXAMPLE 15

[3-[4-(4,5-Diphenyl-2-oxazolyl)-5-pyrazolyl]phenoxy]acetic acid, (16)

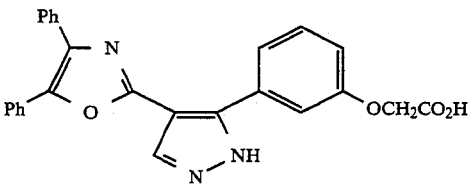

t-Butyl[3-[4-(4,5-diphenyl-2-oxazolyl)-5-pyrazolyl]phenoxy] acetate (230 mg, 0.47 mmol) was dissolved in dichloromethane (4 mL) and trifluoroacetic acid (1 mL) added dropwise. The solution was stirred for about 2 hours, concentrated, triturated with ether, and the resultant solid filtered and washed with ether to give (16) 118 mg (58%), mp 83°-85° C. IR (KBr. cm$^{-1}$) 3250, 3050, 2920, 2500, 1730, 1590, 1440, 1210, 1085, 960, 870, 760, 740, 690. $^1$H NMR (300 MHz, DMSO-d6) δ 4.67 (2H, s) 6.97 to 7.00 (1H, m), 7.32 to 7.64 (14H, m). m/e 438 (MH+).

Anal. Calcd. for C26H19N3O4.0.08 H2O: C, 69.10; H, 4.59; N, 9.30%. Found: C, 68.68; H, 4.17; N, 9.33%.

EXAMPLE 16

Methyl[3-[4-(4,5-diphenyl-2-oxazolyl)-5-pyrazolyl]phenoxy]acetate, (15)

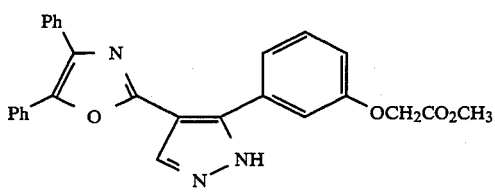

[3-[4-(4,5-diphenyl-2-oxazolyl)-5-pyrazolyl]phenoxy] acetic acid (16) (700 mg, 1.59 mmol) was suspended in methanol (50 mL) and (5 drops) of H2SO4 added. The solution was stirred about 18 hours, concentrated, neutralized with NaHCO3 solution, and extracted into dichloromethane before being dried (MgSO4). Chromatography (elution with 5% methanol/dichloromethane) gave (15) 495 mg (69%). IR (KBr, cm$^{-1}$) 3140, 3060, 2950, 1760, 1740, 1605, 1580, 1440, 1205, 1075, 965, 765, 740, 695. $^1$H NMR (300 MHz, CDCl3) δ 3.74 (3H, s) 4.64 (2H, s), 7.00 to 7.02 (1H, m), 7.30 to 7.54 (11H, m), 7.62 (1H, Br. s), 7.66 to 7.69 (2H, m), 8.22 (1H, s). m/e 452 (MH+).

Anal. Calcd. for C27H21N3O4.0.25 H2O: C, 71.11; H, 4.75; N, 9.21. Found: C, 70.94; H, 4.61; N, 9.19.

EXAMPLE 17

2-[5-(3-Methyoxyphenyl)-4-oxazolyl]-4,5-diphenyloxazole, (28)

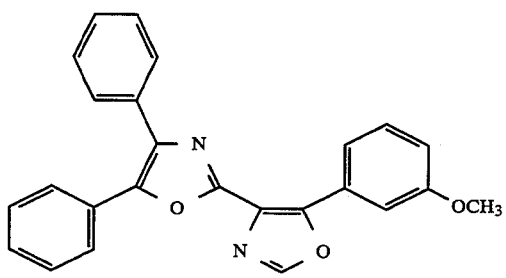

The reaction was performed as above on 4,5-diphenyl-2-oxazolyl-methylisocyanide (27) (3.0 g, 11.5 mmol), m-anisic acid (1.8 g, 11.5 mmol) to obtain upon crystallization (28) 3.0 g (67%), mp 133°–134° C. IR (KBr, cm$^{-1}$) 3440, 3132, 3060, 1602, 1484, 1464, 1434, 1252, 1028, 840, 770, 698. $^1$H NMR (300 MHz, CDCl$_3$) δ 3.81 (1H, s), 6.99 to 7.02 (1H, m), 7.25 to 7.43 (7H, m), 7.68 to 7.76 (4H, m), 7.82 to 7.85 (1H, m), 8.01 (1H, s), 8.28 (1H, Br s). $^{13}$C NMR (75 MHz, CDCl$_3$) ppm 55.73, 112.67, 116.83, 119.85, 124.40, 127.08, 128.30, 128.53, 128.71, 128.99, 129.06, 129.78, 132.46, 136.61, 146.16, 149.93, 150.50, 154.49, 159.89. m/e 395 (MH+).

Anal. Calcd. for C$_{25}$H$_{18}$N$_2$O$_3$: C, 76.13; H, 4.60; N, 7.10. Found: C, 75.71; H, 4.57; N, 7.14.

EXAMPLE 18

2-[5-(3-Methyoxyphenyl)-4-(2-methyloxazolyl]-4,5-diphenyloxazole, (29)

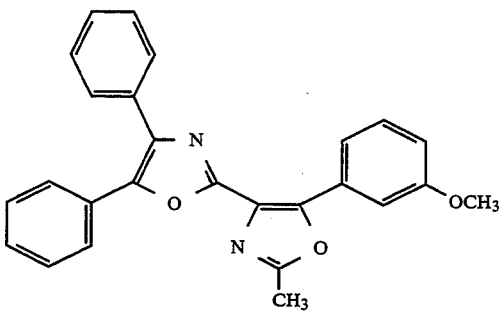

Compound (28) 2-[5-(3-methyoxyphenyl)-4-oxazolyl]-4,5-diphenyloxazole (1.0 g, 2.5 mmol), was dissolved in THF (100 mL) and DMPU (1.4 mL, 3.5 mmol) and cooled to about −78° C. under an atmosphere of N$_2$. To this solution was added dropwise (2.9 mL) of s-butyllithium (1M in hexanes) and the reaction mixture stirred about ½ hour before addition of methyl iodide (0.95 mL, 15 mmol). After about ½ hour at about −78° C., the reaction was allowed to warm to 0° C. and quenched with saturated ammonium chloride solution. Extraction into ether and wash with brine before drying (MgSO$_4$) gave (29) 1 g (97%). Recrystallization from ether/chloroform gave colorless crystals, mp 117°–118° C. IR (KBr, cm$^{-1}$) 3072, 1602, 1590, 1466, 1252, 1094, 1040, 788, 764, 688. $^1$H NMR (300 MHz, CDCl$_3$) δ 2.62 (3H, s), 3.81 (3H, s) 6.95 to 6.99 (1H, m), 7.32 to 7.41 (7H, m), 7.66 to 7.79 (5H, m), 8.18 (1H, Br. s). $^{13}$C NMR (75 MHz, CDCl$_3$) ppm 14.17, 55.71, 112.47, 112.69, 116.33, 116.83, 119.86, 124.66, 127.17, 128.31, 128.45, 128.65, 128.83, 128.98, 129.68, 132.49, 136.58, 145.95, 150.13, 154.81, 159.86, 160.80, m/e 409 (MH+).

Anal. Calcd. for C$_{26}$H$_{20}$N$_2$O$_3$.0.23 H$_2$O: C, 75.70; H, 4.99; N, 6.79; H$_2$O, 0.98%. Found: C, 75.68; H, 4.84; N, 6.75; H$_2$O, 0.67%.

EXAMPLE 19

3-[4-(4,5-Diphenyl-2-oxazolyl)-2-methyl-5-oxazolyl]-phenol

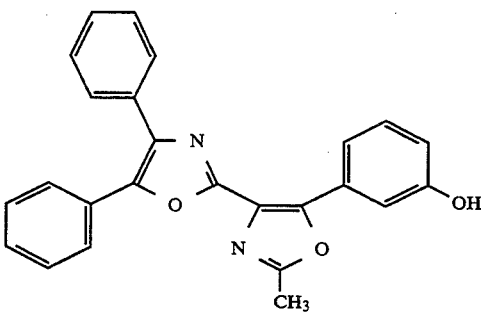

2-[5-(3-Methyoxyphenyl)-4-(2-methyloxazolyl]-4,5-diphenyloxazole (29) (1 g, 2.45 mmol) was dissolved in dichloromethane (50 mL) and cooled to about 0° C. under N$_2$. Boron tribromide solution (10 mL of 1M in dichloromethane) was added dropwise and the solution stirred about 18 hours at room temperature. Methanol (5 mL) was added {caution: reacts vigorously} and after being stirred about 10 minutes the solution was concentrated onto SiO$_2$ and chromatographed (elution with 20% chloroform/diethyl ether) to give 800 mg (83%), mp 93°–99° C. IR (KBr, cm$^{-1}$) 3422, 3240, 3062, 2834, 1592, 1582, 1444, 1276, 1246, 1086, 966, 870, 764, 694. $^1$H NMR (300 MHz, CDCl$_3$) δ 2.49 (3H, s), 6.83 to 6.87 (1H, m), 7.18 to 7.31 (7H, m), 7.53 to 7.57 (3H, m), 7.63 to 7.67 (3H, m). $^{13}$C NMR (75 MHz, CDCl$_3$) ppm 14.05, 114.57, 117.24, 118.84, 124.19, 126.97, 128.23, 128.35, 128.60, 128.78, 128.87, 129.64, 132.34, 136.47, 145.72, 150.38, 154.72, 157.49, 160.75, m/e 395 (MH+).

Anal. Calcd. for C$_{25}$H$_{18}$N$_2$O$_3$.0.65 H$_2$O: C,73.94; H, 4.80; N, 6.90; H$_2$O, 2.88%. Found: C, 73.65; H, 4.67; N, 6.71; H$_2$O, 1.9%.

EXAMPLE 20

Methyl[3-[4-(4,5-diphenyl-2-oxazolyl)-2-methyl-5-oxazolyl]phenoxy]acetate, (23)

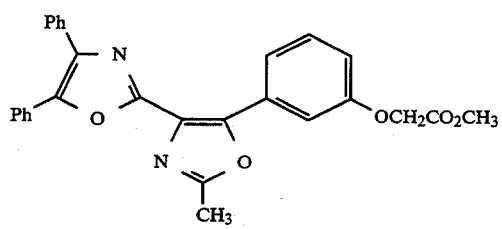

A mixture of 3-[4-(4,5-diphenyl-2-oxazolyl)-2-methyl-5-oxazolyl]phenol (800 mg, 2.0 mmol), methyl bromoacetate (0.38 mL, 4.1 mmol), potassium carbonate (560 mg, 4.1 mmol), and potassium iodide (cat.) was heated at reflux in acetonitrile (80 mL) for about 18 hours. After being cooled to room temperature, the solution was filtered and concentrated to give a solid which was recrystallized from methanol/diethyl ether to give (23) 400 mg (42%), mp 145°–147° C. IR (KBr, cm$^{-1}$) 3440, 3076, 2948, 1766, 1610, 1590, 1442, 1428, 1282, 1250, 1208, 1108, 1088, 770, 694. $^1$H NMR (300 MHz, CDCl$_3$) δ 2.61 (3H, s), 3.75 (3H, s), 4.66 (2H, s), 6.99 to 7.03 (1H, m), 7.33 to 7.43 (7H, m), 7.66 to 7.76 (4H, m), 7.82 to 7.85 (1H, m), 8.24 (1H, Br.s). $^{13}$C NMR (75 MHz, CDCl$_3$) ppm 14.16, 52.39, 65.55, 113.31, 116.80, 120.62, 124.83, 127.18, 128.31, 128.41, 128.75, 128.85, 129.00, 129.89, 132.48, 136.60, 154.71, 157.99, 160.88, 169.30. m/e 467 (MH+).

Anal. Calcd. for $C_{28}H_{22}N_2O_5 \cdot 0.08$ H$_2$O: C, 71.85; H, 5.09; N, 5.99; H$_2$O, 0.35%. Found: C, 71.38; H, 4.81; N, 5.81; H$_2$O, 0.1%.

EXAMPLE 21

[3-[4-(4,5-Diphenyl-2-oxazolyl-2-methyl-5-oxazolyl]-phenoxy]acetic acid, (24)

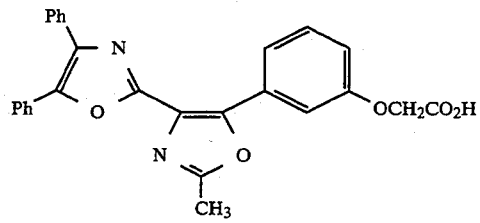

Methyl[3-[4-(4,5-diphenyl-2-oxazolyl)-2-methyl-5-oxazolyl]phenoxy]acetate (23) (200 mg, 0.43 mmol) and lithium hydroxide monohydrate (36 mg, 0.86 mmol) were admixed in DME (20 mL) and heated at reflux for about 18 hours. The lithium carboxylate salt was filtered, suspended in water (40 mL), and acidified with HCl (conc). The resulting solid was filtered and recrystallized from methanol/chloroform to give (24) 180 mg (95%), mp 218°-220° C. IR (KBr, cm$^{-1}$) 3432, 3064, 2910, 1760, 1744, 1722, 1592, 1444, 1208, 1092, 766, 694. $^1$H NMR (300 MHz, DMSO-d$_6$) δ 2.55 (3H, s), 4.72 (2H, s), 7.02 to 7.05 (1H, m), 7.36 to 7.47 (7H, m), 7.58 (2H, d, J=6.3 Hz), 7.66 (2H, d, J=6.8 Hz), 7.77 (1H, d, J=7.9 Hz), 8.03 (1H, Br.s), 13.05 (1H, Br.s). $^{13}$C NMR (75 MHz, DMSO-d$_6$) ppm 13.48, 64.61, 113.43, 115.73, 119.69, 123.80, 126.63, 127.54, 127.92, 128.06, 128.55, 129.07, 129.28, 129.87, 131.60, 135.64, 145.17, 149.05, 154.12, 157.79, 160.86, 169.98, m/e 453 (MH+).

Anal. Calcd. for $C_{27}H_{20}N_2O_5 \cdot 0.85$ H$_2$O: C, 69.33; H, 4.68; N, 5.99; H$_2$O, 3.27%. Found: C, 69.33; H, 4.47; N, 5.88; H$_2$O, 1.81%.

EXAMPLE 22

Methyl[3-[4-(4,5-diphenyl-2-oxazolyl)-2-phenyl-5-oxazolyl]phenoxy]acetate, (25)

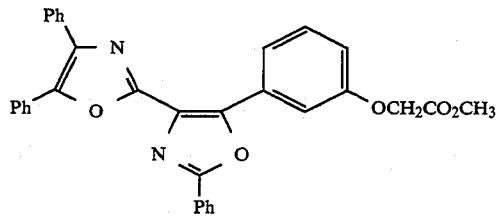

A mixture of 3-[4-(4,5-diphenyl-2-oxazolyl)-2-phenyl-5-oxazolyl]phenol (200 mg, 0.44 mmol), methyl bromoacetate (0.063 mL, 0.6 mmol), potassium carbonate (91 mg, 0.6 mmol), and potassium iodide (cat.) was heated at reflux in acetonitrile (10 mL) for about 18 hours. After being cooled to room temperature, the solution was filtered, concentrated, and chromatographed (elution with 20% ethyl acetate/hexanes) to give (25) 100 mg (44%), mp 142°-143° C. IR (KBr, cm$^{-1}$) 3062, 2952, 1770, 1604, 1584, 1436, 1214, 866, 768, 696. $^1$H NMR (300 MHz, CDCl$_3$) δ 3.76 (3H, s), 4.68 (2H, s), 7.04 (1H, dd, J=8.3 Hz, J=2.0 Hz), 7.33 to 7.53 (10H, m), 7.69 to 7.77 (4H, m), 7.95 (1H, d, J=8.0 Hz), 8.21 to 8.24 (2H, m), 8.32 (1H, Br. s). $^{13}$C-NMR (75 MHz, CDCl$_3$) ppm 52.42, 65.58, 113.68, 116.85, 120.89, 126.26, 126.70, 127.14, 128.39, 128.46, 128.80, 128.89, 129.06, 129.97, 131.25, 132.50, 136.70, 149.80, 154.71, 158.04, 160.61, 161.29. m/e 529 (MH+).

HRMS: calcd. 529.1763 Found 529.1769

EXAMPLE 23

[3-[4-(4,5-Diphenyl-2-oxazolyl)-2-phenyl-5-oxazolyl]-phenoxy]acetic acid, (26)

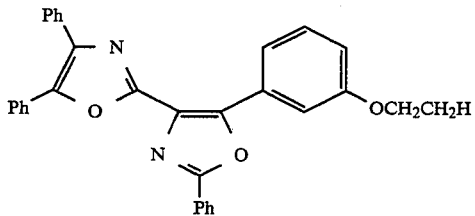

Methyl[3-[4-(4,5-diphenyl-2-oxazolyl)-2-phenyl-5-oxazolyl]phenoxy]acetate (25) (45 mg, 0.09 mmol) and lithium hydroxide monohydrate (6 mg, 0.12 mmol) were admixed in DME (10 mL) and heated at reflux for about 18 hours. The lithium carboxylate salt was filtered, suspended in water (10 mL), and acidified with HCl (conc). The resulting solid was filtered and recrystallized from methanol to give (26) 25 mg (58%), mp —°C. IR (KBr, cm$^{-1}$) 3440, 3064, 2916, 1758, 1578, 1484, 1444, 1196, 1084, 762, 712, 692. $^1$H NMR (300 MHz, DMSO-d$_6$) δ 4.75 (2H, s), 7.08 (1H, dd, J=8.2 Hz, J=2.3 Hz), 7.37 to 7.69 (14H, m), 7.96 (1H, d, J=8.2 Hz), 8.13 to 8.16 (3H, m), 13.07 (1H, Br. s). $^{13}$C-NMR (75 MHz, DMSO-d$_6$) ppm 64.71, 113.79, 116.05, 120.13, 125.22, 125.85, 126.56, 126.81, 127.55, 127.92, 128.56, 128.85, 129.08, 129.27, 129.36, 129.90, 131.43, 131.56, 135.76, 145.43, 149.42, 153.95, 157.84, 159.71, 169.99. m/e 514 (MH+).

Anal. Calcd. for $C_{32}H_{22}N_2O_5 \cdot 0.28$ H$_2$O: C, 74.25; H, 4.35; N, 5.41 H$_2$O, 0.60%. Found: C, 73.97; H, 4.02; N, 5.34; H$_2$O 0.37%.

EXAMPLE 24

Methyl[3-[2-(4,5-diphenyl-2-oxazolyl)-2-(formylamino)-1-hydroxy-ethyl]phenoxy]acetate, (33)

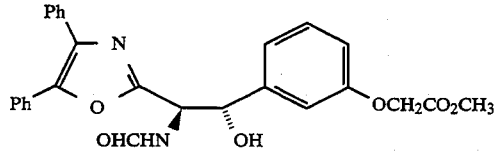

To a mixture of 4,5-diphenyl-2-oxazolylmethylisocyanide (27) (14 g, 54 mmol) and 3-[(methoxycarbonyl)methoxy]benzaldehyde (10.5 g, 54 mmol) dissolved in THF (250 mL) under N$_2$ was added sodium Hydride (2.4 g, 60 mmol of 60% disp.) at room temperature. The reaction mixture was stirred about 18 hours, poured onto dilute 0.1N HCl (1 vol), and after being stirred about 10 minutes was extracted with ethyl acetate, washed with brine, and dried. Chromatography (elution with 10% ethyl acetate/chloroform) gave (33) 4 g (16%) mp 66°-68° C., (plus the other products). IR (KBr, cm$^{-1}$) 3388, 3058, 2952, 1760, 1674, 1604, 1588, 1490, 1444, 1214, 1074, 766, 696. $^1$H NMR (300 MHz, CDCl$_3$) δ 3.75 (3H, s), 4.25 (2H, s), 5.34 (1H, Br. s), 5.58 (1H, dd, J=9.2 Hz, J=2.8 Hz), 6.72 (1H, d, J=9.1 Hz), 6.79 (1H, dd, J=8.0 Hz, 2.2 Hz, 6.96 to 7.02 (2H, m), 7.21 to 7.34 (8H, m), 7.45 to 7.58 (4H, m), 8.09 (1H, s). $^{13}$C-NMR (75 MHz, CDCl$_3$) ppm 50.99, 52.26, 65.27, 73.09, 112.69, 114.00, 119.36, 126.60, 127.83, 127.90, 128.11, 128.45, 128.67, 128.76, 128.92, 129.64, 131.66, 134.80, 140.87, 146.17, 157.86, 160.39, 160.93, 169.35. m/e 473 (MH+).

Anal. Calcd. for C$_{27}$H$_{24}$N$_2$O$_6$: C, 68.63; H, 5.12; N, 5.93. Found: C, 68.78; H, 5.00; N, 5.63.

EXAMPLE 25

[3-[2-(4,5-Diphenyl-2-oxazolyl)-2-(formylamino)ethenyl]phenoxy]acetic acid

To a mixture of 4,5-diphenyl-2-oxazolylmethylisocyanide (27) (5 g, 19 mmol) and 3-[(methoxycarbonly)methoxy]benzaldehyde (3.7 g, 19 mmol) dissolved in THF (65 mL) under N$_2$ was added sodium hydride (1.54 g, 39 mol of 60% disp.) at room temperature. The reaction mixture was stirred about 18 hours, quenched by the addition of water (10 mL), and stirred about 10 minutes. The solution was concentrated, diluted with water, washed with ether, acidified with HCl (conc), and filtered. Chromatography (elution with 70% ethyl acetate/25% hexanes/5% acetic acid) gave (34) 6 g (71%), mp 199°-201° C. for the more polar product; and (31) 2 g (23%) as a foam for the less polar product.

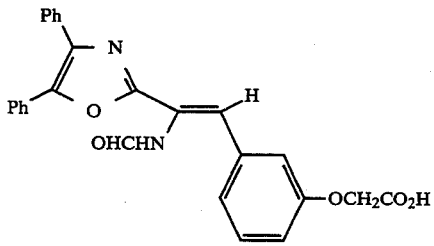

IR (KBr, cm$^{-1}$) 3302, 1736, 1700, 1648, 1630, 1600, 1586, 1522, 1224, 762, 688. $^1$H NMR ( 300 MHz, DMSO-d$_6$) δ 4.70 (2H, s), 6.91 to 6.93 (1H, m), 7.29 to 7.46 (10H, m), 7.58 to 7.65 (4H, m), 8.26 and 8.35 (1H, d and s, J=10.9 Hz), 9.80 and 10.12 (1H, d and s, J=10.8 Hz). $^{13}$C-NMR (75 MHz, DMSO-d$_6$) ppm 64.56, 90.50, 115.24, 115.41, 121.58, 122.59, 126.48, 126.61, 127.73, 128.13, 128.58, 129.11, 129.70, 135.17, 157.86, 158.45, 161.09, 170.20 m/e 441 (MH+).

Anal. Calcd. for C$_{26}$H$_{20}$N$_2$O$_5$.0.05 H$_2$O: C, 70.76; H, 4.59; N, 6.35; H$_2$O, 0.20%. Found: C, 70.15; H, 4.46; N, 6.27; H$_2$O, 0.19%.

Compound 35

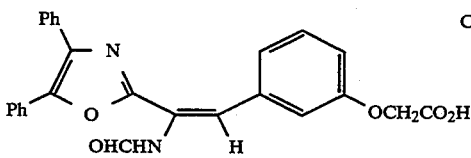

IR (KBr, cm$^{-1}$) 3332, 3058, 2924, 1734, 1692, 1604, 1280, 1230, 1164, 766, 694. $^1$H NMR (300 MHz, DMSO-d$_6$) δ 4.57 (2H, s), 6.81 to 6.93 (3H, m), 7.16 to 7.64 (12H, m), 8.34 to 8.38 and 8.53 (1H, m and d, J=10.3 Hz), 10.05 and 10.15 (1H, d and s, J=10.4 Hz), $^{13}$C-NMR (75 MHz, DMSO-d$_6$) ppm 64.89, 79.26, 113.79, 114.69, 121.38, 122.36, 123.33, 126.46, 127.69, 128.62, 128.82, 129.05, 129.29, 135.59, 136.20, 155.90, 157.82, 160.66, 170.28. m/e 441 (MH+).

Anal. Calcd. for C$_{26}$H$_{20}$N$_2$O$_5$.2.25 H$_2$O: C, 64.93; H, 5.13; N, 5.83; H$_2$O, 8.43%. Found: C, 65.16; H, 4.39; N, 5.55; H$_2$O, 1.79%.

EXAMPLE 26

3-[2-(4,5-Diphenyl-2-oxazolyl)-2-formylamino)-1-hydroxyethyl]phenoxy]acetic acid, (36)

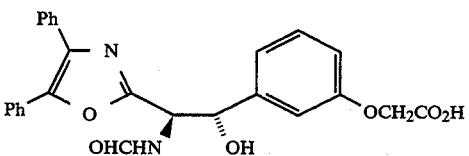

Methyl[3-[4-(4,5-diphenyl-2-oxazolyl)-4,5-dihydro-5-oxazolyl]phenoxy]acetate (31) (600 mg, 1.3 mmol) was dissolved in methanol (100 mL) and 5M NaOH solution (1 mL) was added. The reaction mixture was stirred at room temperature for about 2 hours and acidified with dil. HCl. After being concentrated to remove solvent, the residue was diluted with water, and extacted into ethyl acetate. The organic phase was washed with brine and dried. Purification by recrystallizaton from ether gave (36) as a beige solid, mp 117°-119° C. IR (KBr, cm$^{-1}$) 3396, 3058, 2906, 2556, 1728, 1674, 1228, 1070, 764, 694. $^1$H NMR (300 MHz, DMSO-d$_6$) δ 4.62 (2H, s), 5.18 (H, Br. s), 5.27 (1H, dd, J=8.8 Hz, J=3.9 Hz), 6.04 (1H, Br. s), 6.78 (1H, dd, J=8.1 Hz, J=2.1 Hz), 6.95 to 7.02 (2H, m), 7.22 (1H, t, J=7.9 Hz), 7.32 to 7.56 (10H, m), 8.06 (1H, s), 8.79 ppm (1H, d, J=8.8 Hz). $^{13}$C-NMR (75 MHz, DMSO-d$_6$) ppm 54.17, 66.20, 74.56, 114.41, 114.62, 115.03, 120.82, 128.21, 129.16, 130.01, 130.42, 130.69, 133.61, 136.26, 144.99, 146.62, 159.26, 162.87, 163.07, 171.87. m/e 459 (MH+).

Anal. Calcd. for C$_{26}$H$_{22}$N$_2$O$_6$.0.9 H$_2$O: C, 65.79; H, 5.06; N, 5.91; H$_2$O, 3.42%. Found: C, 65.96; H, 4.75; N, 5.94; H$_2$O, 3.62%.

EXAMPLE 27

[3-[2-(4,5-Diphenyl)-2-oxazolyl)-2-amino-1-hydroxyethyl]phenoxy]acetic acid, (37)

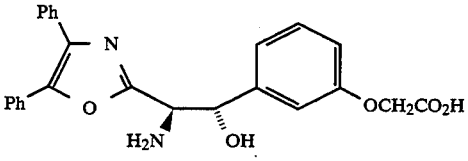

Methyl[3-[2-(4,5-diphenyl-2-oxazolyl) -2-(formylamino)-1-hydroxy-ethyl]phenoxy]acetate (33) (2 g, 4.5 mmol) was dissolved in methanol (60 mL) and 5M NaOH solution (6 mL) was added. The reaction mixture heated at reflux for about ½ hour, concentrated, acidified with HCl (conc), filtered, and washed with ether to give (37) 1.2 g (63%) as a white solid, mp 156°-158° C. IR (KBr, cm$^{-1}$) 3422, 3060, 1732, 1604, 1502, 1248, 1062, 764, 694. $^1$H NMR (300 MHz, DMSO-d$_6$) δ 4.35 to 4.45 (1H, m), 4.5 to 4.6 (2H, m), 4.9 to 5.0 (1H, m), 6.7 to 6.95 (3H, m), 7.15 to 7.25 (1H, m), 7.3 to 7.6 (10H, m). $^{13}$C-NMR (75 MHz, DMSO-d$_6$) ppm 55.05, 55.20, 64.83, 73.34, 73.79, 112.91, 113.54, 113.77, 119.33, 126.43, 126.56, 127.50, 128.00, 128.48, 128.81, 129.06, 129.20, 131.63, 142.65, 145.26, 157.85, 159.74, 170.34. m/e 431 (MH+).

Anal. Calcd. for $C_{25}H_{22}N_2O_5$·0.6 HCl/0.5 H$_2$O: C, 65.09; H, 5.16; N, 6.08; Cl, 4.61; H$_2$O, 1.95%. Found: C, 64.64; H, 5.03; N, 5.85; Cl, 4.79; H$_2$O, 1.93%.

EXAMPLE 28

Methyl[3-[2-(4,5-diphenyl-2-oxazolyl)-2-amino-1-hydroxyethyl]phenoxy]acetate, (38)

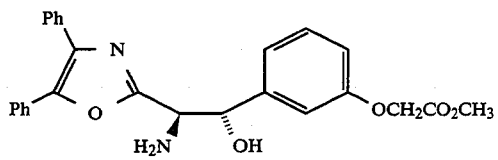

[3-[2-(4,5-Diphenyl-2-oxazolyl)-2-amino-1-hydroxyethyl]phenoxy]acetic acid (37) (2 g, 4.5 mmol) was dissolved in 3% H$_2$SO$_4$ methanol solution and stirred about 18 hours at room temperature. The reaction mixture was neutralized with NaHCO$_3$ solution, concentrated, and extracted with ether. The organic layers were washed with brine, and dried. Chromatography (elution with 70% ethyl acetate/chloroform) and recrystallization from diethyl ether gave (38) 1.5 g (74%) mp 121°–122.5° C. IR (KBr, cm$^{-1}$) 3352, 3152, 2950, 1750, 1586, 1446, 1218, 1142, 766, 696. $^1$H NMR (300 MHz, CDCl$_3$) δ 3.78 (3H, s), 4.17 (1H, d, J=5.0 Hz), 4.61 (2H, s), 5.8 (1H, d, J=5.0 Hz), 6.83 to 6.87 (1H, m), 6.99 to 7.01 (2H, m), 7.25 to 7.41 (7H, m), 7.48 to 7.50 (2H, m), 7.62 to 7.65 (2H, m). $^{13}$C-NMR (75 MHz, CDCl$_3$) ppm 52.22, 56.08, 65.32, 112.65, 114.11, 119.73, 126.63, 127.87, 128.25, 128.61, 128.64, 128.71, 129.58, 132.04, 134.90, 142.36, 145.62, 157.93, 163.22, 169.30. m/e 445 (MH+).

Anal. Calcd. for $C_{26}H_{24}N_2O_5$·0.13 H$_2$O: C, 69.90; H, 5.48; N, 6.27; H$_2$O, 0.52%. Found: C, 70.31; H, 5.61; N, 6.33; H$_2$O, 0.55%.

EXAMPLE 29

Methyl[3-[4-(4,5-diphenyl-2-oxazolyl)-4,5-dihydro-5-oxazolyl]phenoxy]acetate, (31)

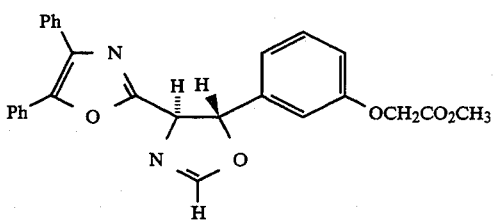

Methyl[3-[2-(4,5-diphenyl-2-oxazolyl)-2-amino-1-hydroxyethyl]phenoxy]acetate (38) (300 mg, 0.68 mmol) was stirred together with trimethylorthoformate (0.34 mL, 2.02 mmol) and p-TsOH (cat.) under Dean-Stark conditions for about 1 hour. Concentration onto SiO$_2$ and chromatography (elution with 5% ethyl acetate/chloroform) gave (31) as an oil. IR (KBr, cm$^{-1}$) 3060, 2952, 1760, 1626, 1444, 1212, 1102, 766, 694. $^1$H NMR (300 MHz, C$_6$D$_6$) δ 3.19 (3H, s), 4.09 (2H, s), 5.17 (1H, dd, J=8.0 Hz, J=2.2 Hz), 6.08 (1H, d, J=8.0 Hz), 6.52 (1H, d, J=2.1 Hz), 6.61 to 6.65 (1H, m), 6.80 to 7.12 (9H, m), 7.50 to 7.53 (2H, m), 7.77 to 7.80 (2H, m). $^{13}$C-NMR (75 MHz, C$_6$D$_6$) ppm 52.11, 65.83, 72.47, 83.74, 96.61, 111.15, 115.46, 119.62, 127.93, 128.38, 128.70, 129.03, 129.24, 129.48, 129.54, 129.97, 131.10, 133.63, 142.22, 147.81, 156.55, 159.55, 162.02, 169.26. m/e 455 (MH+);

Anal. Calcd. for $C_{27}H_{22}N_2O_5$: C, 71.36; H, 4.87; N, 6.16. Found: C, 72.31; H, 4.85; N, 5.56.

EXAMPLE 30

Methyl[3-[4-(4,5-diphenyl-2-oxazolyl)-4,5-dihydro-2-methyl-5-oxazolyl]phenoxy]acetate, (39) and (41)

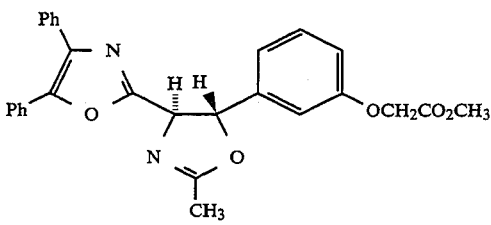

Methyl[3-[2-(4,5-diphenyl-2-oxazolyl)-2-amino-1-hydroxyethyl]phenoxy]acetate (38) (2.5 g, 5.6 mmol) (cis and trans mixture), trimethylortho acetate (2.1 mL, 16 mmol), and p-TsOH (cat.) were stirred together under Dean-Stark conditions for about ½ hour. Concentration and separation by chromatography (elution with 20% ethyl acetate/chloroform) gave (39) and (41) both oils.

Compound 39

IR (NaCl film, cm$^{-1}$) 3058, 2952, 1762, 1742, 1668, 1444, 1216, 1162, 766, 694, 674. $^1$H NMR (300 MHz, CDCl$_3$) δ 2.18 (3H, d, J=1.4 Hz), 3.78 (3H, s) 4.65 (2H, s), 5.19(1H, dd, J=8.0 Hz, J=1.4 Hz), 6.02 (1H, d, J=8.0 Hz), 6.84 to 6.88(1H, m), 6.98 (1H, Br. s), 7.03 to 7.05 (1H, m), 7.30 to 7.40 (7H, m), 7.58 to 7.62 (2H, m), 7.65 to 7.68 (2H, m). $^{13}$C-NMR (75 MHz, CDCl$_3$) ppm 14.05, 52.17, 62.51, 71.88, 83.83, 112.21, 114.13, 118.79, 126.66, 127.92, 128.08, 128.45, 128.50, 128.61, 130.12, 132.11, 135.32, 114.14, 146.55, 158.07, 160.75, 166.74, 169.00. m/e 469 (MH+).

Anal. Calcd. for $C_{28}H_{24}N_2O_5$·0.65 H$_2$O: C, 70.04; H, 5.31; N, 5.84; H$_2$O, 2.43%. Found: C, 69.99; H, 5.20; N, 5.61; H$_2$O, 2.19%.

Compound 42

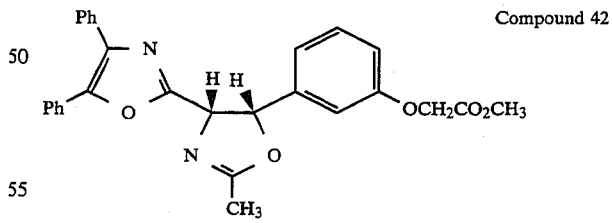

IR (NaCl film, cm$^{-1}$) 3060, 2952, 1760, 1742, 1672, 1444, 1214, 1162, 766, 694. $^1$H NMR (300 MHz, CDCl$_3$) δ 2.27 (3H, d, J=1.3 Hz), 3.69 (3H, s) 4.34 (2H, s), 5.75 (1H, dd, J=10.4 Hz, J=1.3 Hz), 5.85 (1H, d, J=10.4 Hz), 6.69 (1H, dd, J=8.0 Hz, J=2.3 Hz), 6.76 (1H, Br. s), 6.84 (1H, d, J=7.7 Hz), 7.12 (1H, t, J=7.9 Hz) 7.19 to 7.43 (10H, m). $^{13}$C-NMR (75 MHz, CDCl$_3$) ppm 14.15, 52.00, 65.11, 69.27, 82.88, 111.77, 114.44, 119.08, 125.68, 127.69, 127.82, 128.30, 128.41, 128.56, 129.13, 132.00, 134.72, 137.74, 145.87, 157.54, 158.56, 167.86, 168.85. m/e 469 (MH+).

Anal. Calcd. for $C_{28}H_{24}N_2O_5 \cdot 0.7\ H_2O$: C, 69.91; H, 5.33; N, 5.83; $H_2O$, 2.62%. Found: C, 69.89; H, 5.02; N, 5.68; $H_2O$, 2.81%.

EXAMPLE 31

Methyl[3-[4-(4,5-diphenyl-2-oxazolyl)-4,5-dihydro-2-phenyl-5-oxazolyl]phenoxy]acetate, (39) & (42)

Methyl[3-[2-(4,5-diphenyl-2-oxazolyl)-2-amino-1-hydroxyethyl]phenoxy]acetate (38) (600 mg, 1.4 mmol) (cis and trans mixture), trimethylortho benzoate (0.56 mL, 3.5 mmol), and p-TsOH (cat.) were stirred together under Dean-Stark conditions for about 2.5 hours. Concentration and separation by chromatography (elution with 5% ethyl acetate/chloroform) gave (39) as an oil for the more polar product; and (42) oil, for the less polar product.

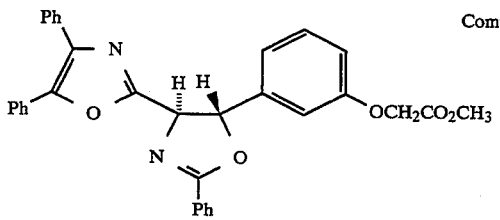

Compound 39

IR (Film, $cm^{-1}$) 3060, 2952, 1762, 1742, 1644, 1450, 1212, 1086, 1066, 766, 694. $^1H$ NMR (300 MHz, $CDCl_3$) δ 3.76 (3H, s), 4.64 (2H, s), 5.42 (3H, d, J=8.1 Hz), 6.20 (1H, d, J=8.1 Hz), 6.86 to 6.90 (1H, m), 7.03 (1H, Br, s), 7.10 (1H, d, J=7.8 Hz), 7.31 to 7.69 (14H, m), 8.08 to 8.11 (1H, m). m/e 531 (MH+).

Anal. Calcd. for $C_{33}H_{26}N_2O_5 \cdot 2.45\ H_2O$: C, 68.96; H, 5.42; N, 4.88; $H_2O$, 7.68%. Found: C, 68.94; H, 4.71; N, 4.45%; $H_2O$ 7.5%.

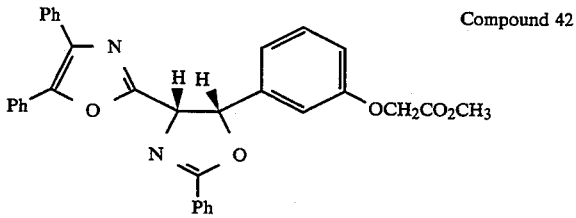

Compound 42

IR (NaCl film, $cm^{-1}$) 3060, 2952, 1762, 1745, 1652, 1496, 1448, 1212, 1064, 764, 694. $^1H$ NMR (300 MH, $CDCl_3$) δ 3.66 (3H, s), 4.33 (2H, s), 6.00 (1H, d, J=10.4 Hz), 6.07 (1H, d, J=10.4 Hz), 6.07 to 6.72. (1H, m), 6.91 (1H, d, J=7.7 Hz), 7.12 to 7.87 (14H, m), 8.14 to 8.17 (2H, m). $^{13}C$-NMR (75 MHz, $CDCl_3$) ppm 51.98, 65.08, 69.60, 82.84, 111.67, 114.56, 119.10, 126.56, 127.68, 127.84, 128.28, 128.33, 128.46, 128.73, 129.21, 132.09, 137.86, 157.56, 166.28. m/e 531 (MH+).

EXAMPLE 32

Methyl[3-[4-(4,5-diphenyl-2-oxazolyl)-2-oxo-5-oxazolidinyl]phenoxy]acetate, (43)

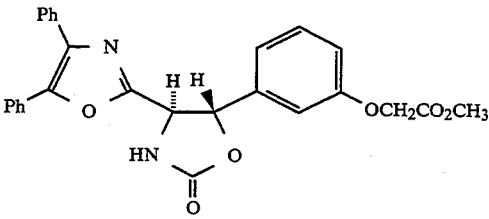

A mixture of methyl[3-[2-(4,5-diphenyl-2-oxazolyl)-2-amino-1-hydroxyethyl]phenoxy]acetate (38) (1 g, 2.25 mmol) and triphosgene (831 mg, 2.8 mmol) was dissolved in THF (25 mL) and heated at about 60° C. while sparging with $N_2$ for about 1 hour. The reaction mixture was concentrated and chromatographed (elution with 20% ethyl acetate/benzene) to give (43) 900 mg (90%) as an amorphous solid, mp 55°-65° C. IR (Film, $cm^{-1}$) 3286, 3066, 2954, 1762, 1604, 1590, 1444, 1214, 764, 694. $^1H$ NMR (300 MHz, $CDCl_3$) δ 3.79 (3H, s), 4.66 (2H, s), 4.96 (1H, d, J=5.9 Hz), 5.94 (1H, d, J=5.9 Hz), 6.55 (1H, Br.s), 6.91 to 6.94 (1H, m), 7.06 to 7.12 (2H, m), 7.32 to 7.66 (11H, m). $^{13}C$-NMR (75 MHz, $CDCl_3$) ppm 52.29, 57.50, 65.27, 80.42, 112.01, 115.17, 118.74, 126.74, 127.86, 128.06, 128.31, 128.53, 128.68, 128.80, 129.19, 130.40, 131.53, 139.21, 147.15, 157.90, 158.68, 169.04. m/e 471 (MH+).

Anal. Calcd. for $C_{27}H_{22}N_2O_6 \cdot 0.6\ H_2O$: C, 67.38; H, 4.86; N, 5.82; $H_2O$, 2.25%. Found: C, 67.03; H, 4.67; N, 5.75; $H_2O$ 0.31%.

EXAMPLE 33

[3-[4-(4,5-Diphenyl-2-oxazolyl)-2-oxo-5-oxazolidinyl]phenoxy]acetic acid (44) and (45)

Methyl [3-[4-(4,5-diphenyl-2-oxazolyl)-2-oxo-5-oxazolidinyl]phenoxy]acetate (43) (1 g, 2.2 mmol) (cis and trans mixture) was dissolved in methanol (100 mL) and 5M NaOH solution (0.4 mL) added. The reaction mixture was stirred at room temperature for about ½ hour and concentrated to remove solvent. The residue was diluted with water and acidified before extaction into ethyl acetate. The organic phase was washed with brine and dried. Separation by radial chromatography (elution with 50% ethyl acetate/45% hexanes/5% acetic acid) gave (44) 800 mg as a white solid, mp 82°-85° C. for the more polar product; and (45) as a white solid, mp 100°-109° C. for the less polar product.

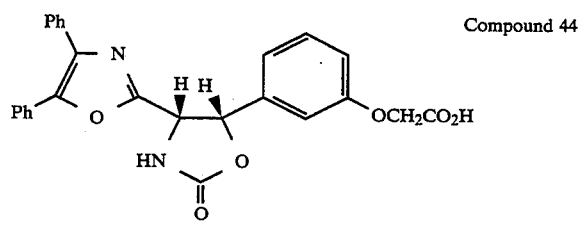

Compound 44

IR (Film, $cm^{-1}$) 3410, 3070, 2930, 1755, 1605, 1495, 1445, 1220, 765, 695. $^1H$ NMR (300 MHz, DMSO-$d_6$) δ 4.37 (2H, Br. s), 5.43 (1H, d, J=8.1 Hz), 5.98 (1H, d, J=8.0 Hz), 6.70 to 6.76 (3H, m), 7.09 to 7.32 (11H, m), 7.84 (1H, s). $^{13}$C NMR (75 MHz, DMSO-d$_6$) ppm 55.21, 64.98, 78.81, 112.28, 114.35, 118.22, 125.39, 126.54, 127.33, 127.82, 128.88, 128.35, 128.74, 128.98, 129.17, 129.27, 131.51, 134.39, 136.36, 145.63, 157.85, 158.26, 158.94. m/e 457 (MH+). m/e 457 (MH+).

Anal. Calcd. for C$_{26}$H$_{20}$N$_2$O$_6$: C, 68.41; H, 4.41; N, 6.14%. Found: C, 68.32; H, 4.50; N, 5.62%.

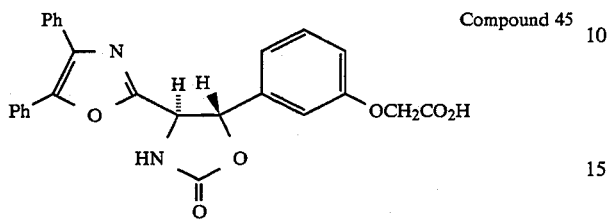

Compound 45

IR (KBr, cm$^{-1}$) 3270, 3070, 2930, 1755, 1604, 1490, 1445, 1215, 1030, 765, 695. $^1$H NMR (300 MHz, DMSO-d$_6$) δ 4.71 (2H, s), 5.08 (1H, d, J=5.5 Hz), 5.89 (1H, d, J=5.5 Hz), 6.94 to 6.97 (1H, m), 7.06 to 7.09 (2H, m), 7.35 to 7.51 (7H, m), 7.58 to 7.61 (4H, m), 8.75 (1H, s). $^{13}$C-NMR (75 MHz, DMSO-d$_6$) ppm 56.67, 64.66, 79.31, 112.55, 114.96, 118.72, 126.79, 127.51, 128.04, 128.28, 128.59, 128.88, 128.98, 129.16, 129.45, 130.20, 131.51, 134.79, 139.64, 146.20, 157.53, 158.20, 160.16, 170.16. m/e 457 (MH+).

Anal. Calcd. for C$_{26}$H$_{20}$N$_2$O$_6$·0.1 AcOH/0.3H$_2$O: C, 67.27; H, 4.53; N, 5.99; H$_2$O, 1.16%. Found: C, 65.49; H, 4.35; N, 5.46; H$_2$O, 1.12%.

EXAMPLE 34

4,5-Diphenyl-2-oxazolyl-methylformamide

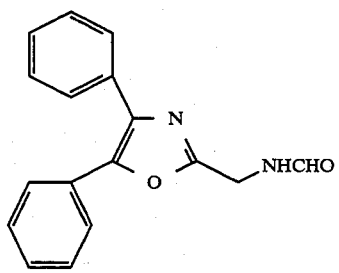

Benzyl [(4,5-diphenyl-2-oxazolyl)methyl]carbamate (Wasserman et al., *Chem. Rev.*, 86: 845 (1986)) (56 g, 0.15 mol) was added to a suspension of 10% palladium on carbon (16 g) in 1.5 L of 5% solution formic acid in methanol. The reaction mixture was stirred about 18 hours, filtered through a celite pad, and concentrated. The residual oil was taken up in toluene (500 mL) and ethyl formate (100) and heated at about 70° C. for about 2.5 hours. After being diluted with ethyl acetate (1 vol) the solution was washed with saturated sodium bicarbonate solution, brine, and dried (Na$_2$SO$_4$). Concentrated gave 38 g (94%) of product. IR (KBr, cm$^{-1}$) 3288, 1658, 1502, 1366, 1206, 1062, 766, 694. $^1$H NMR (300 MHz, CDCl$_3$) δ 4.66 (2H, d, J=5.5H$_3$), 6.90 (1H, brs), 7.28 to 7.38 (6H, m), 7.50 to 7.62 (4H, m), 8.26 (1H, s); $^{13}$C NMR (75 MHz, CDCl$_3$) ppm 35.43, 126.53, 126.58, 127.81, 127.90, 128.34, 128.41, 128.70, 128.72, 128.86, 128.98, 131.92, 135.09, 146.29, 158.81, 161.15; m/e 279 (MH+).

Anal. Calcd for C$_{17}$H$_{14}$N$_2$O$_2$: C, 73.37; H, 5.07; N, 10.07. Found: C, 73.19; H, 4.90; N, 10.14.

EXAMPLE 35

4,5-Diphenyl-2-oxazolyl-methylisocyanide, (27)

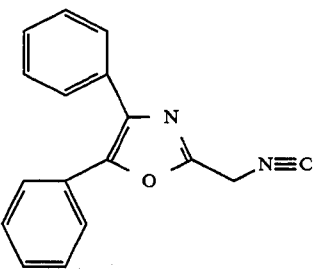

4,5-Diphenyl-2-oxazolyl-methylformamide (14 g, 0.05 mol) was dissolved in dichloromethane (70 mL)/triethylamine (16 mL) and cooled to about 0° C. under N$_2$. Upon dropwise addition of phosphorous oxychloride (4.7 mL, 0.05 mol), the reaction mixture was warmed to about 25° C. and stirred about 1 hour. A 40% sodium carbonate solution (50 mL) was added and after about 15 minutes the reaction mixture was diluted with water (1 vol), extracted with dichloromethane, washed with saturated sodium carbonate solution, brine and dried (Na$_2$SO$_4$) to give 13 g (98%) of 27 as a white solid. Recrystallization from ether gave light amber colored crystals, mp 95°–96° C. IR (KBr, cm$^{-1}$) 2970, 2956, 2160 (NC), 1604, 1594, 1502, 1446, 1338, 1212, 1054, 1026, 954, 916, 778, 764, 712, 694, 674, 654, 526. $^1$H NMR (300 MHz, CDCl$_3$) δ 4.81 (2H, s), 7.31 to 7.41 (7H, m), 7.57 to 7.66 (5H, m). $^{13}$C NMR (75 MHz, CDCl$_3$) ppm 39.03, 126.78, 127.86, 128.04, 128.58, 128.73, 128.83, 129.25, 131.53, 135.77, 147.28, 153.17, 160.84. m/e 261 (MH+).

Anal. Calcd. for C$_{17}$H$_{14}$N$_2$O: C, 78.44; H, 4.65; N, 10.76. Found: C, 78.38; H, 4.56; N, 10.74.

What is claimed is:

1. A compound of the formula

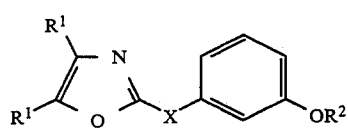

FORMULA I wherein

X is

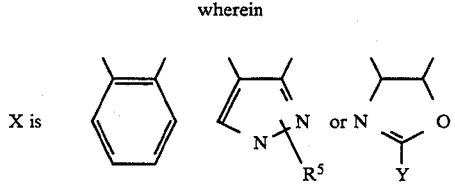

Y is CH$_3$, Ph, or OH, provided that when Y is OH, the compound exists in the keto-enol tautaumerism form

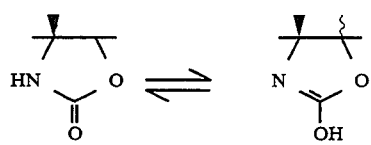

R$^1$ is Ph or Th;

R$^2$ is H or CH$_2$R$^3$;

$R^3$ is H, $OCH_3$, $C_1$–$C_5$ lower alkyl, or $CO_2R^4$;
$R^4$ is H or $C_1$–$C_5$ lower alkyl;
$R^5$ is H or $CH_3$;
or pharmaceutically acceptable salt thereof.

2. The compound of claim 1 which is methyl[2'-(4,5-diphenyl-2-oxazolyl)-[1,1'-biphenyl]-3-yloxy]acetate.

3. The compound of claim 1 which is [2'-(4,5-diphenyl-2-oxazolyl)-[1,1'-biphenyl]-3-yloxy]acetic acid.

4. The compound of claim 1 which is methyl 3-[4-(4,5-diphenyl-2-oxazolyl)-1-methyl-3-pyrazolyl]-phenoxy]acetate.

5. The compound of claim 1 which is methyl[3-[4-(4,5-diphenyl-2-oxazolyl)-1-methyl-5-pyrazolyl]-phenoxy]acetate.

6. The compound of claim 1 which is 3-[4-(4,5-diphenyl-2-oxazolyl)-1-methyl-3-pyrazolyl]phenoxy]acetic acid.

7. The compound of claim 1 which is 3-[4-(4,5-diphenyl-2-oxazolyl)-1-methyl-5-pyrazolyl]phenoxy]acetic acid.

8. The compound of claim 1 is which is 1,1-dimethylethyl-[3-[4-(4,5-diphenyl-2-oxazolyl)-5-pyrazolyl]-phenoxy]acetate.

9. The compound of claim 1 which is [3-[4-(4,5-diphenyl-2-oxazolyl)-5-pyrazolyl]phenoxy]acetic acid.

10. The compound of claim 1 which is methyl[3-[4-(4,5-diphenyl-2-oxazolyl)-5-pyrazolyl]phenoxy]acetate.

11. The compound of claim 1 which is 2-[5-(3-methyoxyphenyl)-4-(2-methyloxazolyl]-4,5-diphenyloxazole.

12. The compound of claim 1 which is methyl[3-[4-(4,5-diphenyl-2-oxazolyl)-2-methyl-5-oxazolyl]-phenoxy]acetate.

13. The compound of claim 1 which is [3-[4-(4,5-diphenyl-2-oxazolyl)-2-methyl-5-oxazolyl]phenoxy]acetic acid.

14. The compound of claim 1 which is methyl[3-[4-(4,5-diphenyl-2-oxazolyl)-2-phenyl-5-oxazolyl]-phenoxy]acetate.

15. The compound of claim 1 which is [3-[4-(4,5-diphenyl-2-oxazolyl)-2-phenyl-5-oxazolyl]phenoxy]acetic acid.

16. The compound of claim 1 which is methyl[3-[4-(4,5-diphenyl-2-oxazolyl)-4,5-dihydro-5-oxazolyl]-phenoxy]acetate.

17. The compound of claim 1 which is methyl[3-[4-(4,5-diphenyl-2-oxazolyl)-4,5-dihydro-2-methyl-5-oxazolyl]phenoxy]acetate.

18. The compound of claim 1 which is methyl[3-[4-(4,5-diphenyl-2-oxazolyl)-4,5-dihydro-2-phenyl-5-oxazolyl]phenoxy]acetate.

19. The compound of claim 1 which is methyl[3-[4-(4,5-diphenyl-2-oxazolyl)-2-oxo-5-oxazolidinyl]-phenoxy]acetate.

20. The compound of claim 1 which is [3-[4-(4,5-diphenyl-2-oxazolyl)-2-oxo-5-oxazolidinyl]phenoxy]acetic acid.

21. The intermediate methyl 4,5-diphenyl-2-oxazole carboxylate.

22. The intermediate 2'-(4,5-diphenyl-2-oxazolyl)-[1,1'-biphenyl-3-ol].

23. The intermediate 3-[4-(4,5-diphenyl-2-oxazolyl)-[1-methylpyrazolyl]phenol.

24. The intermediate 1-[3-hydroxyphenyl]-2-[(dimethylamino)methylene]-2-(4,5-diphenyl-2-oxazolyl)ethanone.

25. The intermediate 1,1-dimethylethyl-[3-[3-[(dimethylamino)methylene]-2-(4,5-diphenyl-2-oxazolyl)-1-oxo-2-propenyl]phenoxy]acetate.

26. The intermediate 2-[5-(3-methyoxyphenyl)-4-oxazolyl]-4,5-diphenyloxazole.

27. The intermediate 3-[4-(4,5-diphenyl-2-oxazolyl)-2-methyl-5-oxazolyl]phenol.

28. The intermediate 1,1-dimethylethyl-[3-[4-(4,5-diphenyl-2-oxazolyl)-5-pyrazolyl]phenoxy]acetate.

29. A method for inhibiting blood platelet aggregation in a mammal which comprises administering a therapeutically effective amount of a compound of claim 1 or a pharmaceutically acceptable salt thereof.

30. The pharmaceutical composition for inhibiting blood platelet aggregation comprising a therapeutically effective amount of a compound of claim 1 of a pharmaceutically acceptable acid addition salt thereof and a pharmaceutical carrier.

* * * * *